US011891654B2

(12) United States Patent
Alvarado Martinez et al.

(10) Patent No.: US 11,891,654 B2
(45) Date of Patent: Feb. 6, 2024

(54) METHODS OF MAKING GENE EXPRESSION LIBRARIES

(71) Applicant: 10x Genomics, Inc., Pleasanton, CA (US)

(72) Inventors: Luigi Jhon Alvarado Martinez, Pleasanton, CA (US); Eswar Prasad Ramachandran Iyer, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 239 days.

(21) Appl. No.: 17/184,117

(22) Filed: Feb. 24, 2021

(65) Prior Publication Data

US 2021/0262019 A1 Aug. 26, 2021

Related U.S. Application Data

(60) Provisional application No. 62/980,867, filed on Feb. 24, 2020.

(51) Int. Cl.
*C12Q 1/6837* (2018.01)
*C12Q 1/6816* (2018.01)
*C12Q 1/6827* (2018.01)

(52) U.S. Cl.
CPC ......... *C12Q 1/6837* (2013.01); *C12Q 1/6816* (2013.01); *C12Q 1/6827* (2013.01); *C12Q 2543/101* (2013.01); *C12Q 2565/514* (2013.01)

(58) Field of Classification Search
CPC ................................................ C12Q 2543/101
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,928,906 A | 7/1999 | Koester et al. |
| 5,958,775 A | 9/1999 | Wickstrrom |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

U.S. Appl. No. 16/353,937, filed Mar. 14, 2019, Frisen et al.

(Continued)

*Primary Examiner* — Teresa E Strzelecka
(74) *Attorney, Agent, or Firm* — Fish & Richardson P.C.

(57) ABSTRACT

Provided herein are methods of determining a location of a target nucleic acid in a biological sample.

16 Claims, 7 Drawing Sheets

(56) References Cited

U.S. PATENT DOCUMENTS

| | | | |
|---|---|---|---|
| 6,800,453 | B2 | 10/2004 | Labaer |
| 6,812,005 | B2 | 11/2004 | Fan et al. |
| 6,828,100 | B1 | 12/2004 | Ronaghi |
| 6,833,246 | B2 | 12/2004 | Balasubramanian |
| 6,852,487 | B1 | 2/2005 | Barany et al. |
| 6,859,570 | B2 | 2/2005 | Walt |
| 6,864,052 | B1 | 3/2005 | Drmanac |
| 6,867,028 | B2 | 3/2005 | Janulaitis |
| 6,872,816 | B1 | 3/2005 | Hall et al. |
| 6,875,572 | B2 | 4/2005 | Prudent et al. |
| 6,890,741 | B2 | 5/2005 | Fan et al. |
| 6,897,023 | B2 | 5/2005 | Fu |
| 6,913,881 | B1 | 7/2005 | Aizenstein et al. |
| 6,942,968 | B1 | 9/2005 | Dickinson et al. |
| 7,011,944 | B2 | 3/2006 | Prudent et al. |
| 7,057,026 | B2 | 6/2006 | Barnes |
| 7,083,980 | B2 | 8/2006 | Reznikoff et al. |
| 7,115,400 | B1 | 10/2006 | Adessi |
| 7,118,883 | B2 | 10/2006 | Inoue |
| 7,166,431 | B2 | 1/2007 | Chee et al. |
| 7,192,735 | B2 | 3/2007 | Lambalot |
| 7,211,414 | B2 | 5/2007 | Hardin |
| 7,255,994 | B2 | 8/2007 | Lao |
| 7,258,976 | B2 | 8/2007 | Mitsuhashi |
| 7,282,328 | B2 | 10/2007 | Kong et al. |
| 7,297,518 | B2 | 11/2007 | Quake |
| 7,329,492 | B2 | 2/2008 | Hardin |
| 7,358,047 | B2 | 4/2008 | Hafner et al. |
| 7,361,488 | B2 | 4/2008 | Fan et al. |
| 7,378,242 | B2 | 5/2008 | Hurt |
| 7,393,665 | B2 | 7/2008 | Brenner |
| 7,405,281 | B2 | 7/2008 | Xu |
| 7,407,757 | B2 | 8/2008 | Brenner |
| 7,473,767 | B2 | 1/2009 | Dimitrov |
| 7,537,897 | B2 | 5/2009 | Brenner |
| 7,563,576 | B2 | 7/2009 | Chee |
| 7,579,153 | B2 | 8/2009 | Brenner |
| 7,582,420 | B2 | 9/2009 | Oliphant et al. |
| 7,601,498 | B2 | 10/2009 | Mao |
| 7,608,434 | B2 | 10/2009 | Reznikoff et al. |
| 7,611,869 | B2 | 11/2009 | Fan |
| 7,635,566 | B2 | 12/2009 | Brenner |
| 7,666,612 | B2 | 2/2010 | Johnsson |
| 7,674,752 | B2 | 3/2010 | He |
| 7,709,198 | B2 | 5/2010 | Luo et al. |
| 7,776,547 | B2 | 8/2010 | Roth |
| 7,776,567 | B2 | 8/2010 | Mao |
| 7,803,943 | B2 | 9/2010 | Mao |
| 7,888,009 | B2 | 2/2011 | Barany et al. |
| 7,892,747 | B2 | 2/2011 | Barany et al. |
| 7,910,304 | B2 | 3/2011 | Drmanac |
| 7,914,981 | B2 | 3/2011 | Barany et al. |
| 7,955,794 | B2 | 6/2011 | Shen et al. |
| 7,960,119 | B2 | 6/2011 | Chee |
| 7,985,565 | B2 | 7/2011 | Mayer et al. |
| 8,003,354 | B2 | 8/2011 | Shen et al. |
| 8,076,063 | B2 | 12/2011 | Fan |
| 8,092,784 | B2 | 1/2012 | Mao |
| 8,148,068 | B2 | 4/2012 | Brenner |
| 8,206,917 | B2 | 6/2012 | Chee |
| 8,268,554 | B2 | 9/2012 | Schallmeiner |
| 8,288,103 | B2 | 10/2012 | Oliphant |
| 8,288,122 | B2 | 10/2012 | O'Leary et al. |
| 8,383,338 | B2 | 2/2013 | Kitzman |
| 8,431,691 | B2 | 4/2013 | McKernan et al. |
| 8,460,865 | B2 | 6/2013 | Chee |
| 8,481,257 | B2 | 7/2013 | Van Eijk |
| 8,481,258 | B2 | 7/2013 | Church et al. |
| 8,481,292 | B2 | 7/2013 | Casbon |
| 8,481,698 | B2 | 7/2013 | Lieberman et al. |
| 8,507,204 | B2 | 8/2013 | Pierce et al. |
| 8,519,115 | B2 | 8/2013 | Webster et al. |
| 8,551,710 | B2 | 10/2013 | Bernitz et al. |
| 8,568,979 | B2 | 10/2013 | Stuelpnagel et al. |
| RE44,596 | E | 11/2013 | Stroun et al. |
| 8,586,310 | B2 | 11/2013 | Mitra |
| 8,597,891 | B2 | 12/2013 | Barany et al. |
| 8,603,743 | B2 | 12/2013 | Liu et al. |
| 8,604,182 | B2 | 12/2013 | Luo et al. |
| 8,614,073 | B2 | 12/2013 | Van Eijk |
| 8,624,016 | B2 | 1/2014 | Barany et al. |
| 8,685,889 | B2 | 4/2014 | Van Eijk |
| 8,741,564 | B2 | 6/2014 | Seligmann |
| 8,741,606 | B2 | 6/2014 | Casbon |
| 8,771,950 | B2 | 7/2014 | Church et al. |
| 8,785,353 | B2 | 7/2014 | Van Eijk |
| 8,790,873 | B2 | 7/2014 | Namsaraev et al. |
| 8,809,238 | B2 | 8/2014 | Livak et al. |
| 8,815,512 | B2 | 8/2014 | Van Eijk |
| 8,835,358 | B2 | 9/2014 | Fodor |
| 8,865,410 | B2 | 10/2014 | Shendure |
| 8,906,626 | B2 | 12/2014 | Oliphant et al. |
| 8,911,945 | B2 | 12/2014 | Van Eijk |
| 8,936,912 | B2 | 1/2015 | Mitra |
| 8,951,726 | B2 | 2/2015 | Luo et al. |
| 8,951,728 | B2 | 2/2015 | Rasmussen |
| 8,986,926 | B2 | 3/2015 | Ferree et al. |
| 9,005,891 | B2 | 4/2015 | Sinicropi et al. |
| 9,023,768 | B2 | 5/2015 | Van Eijk |
| 9,062,348 | B1 | 6/2015 | Van Eijk |
| 9,080,210 | B2 | 7/2015 | Van Eijk |
| 9,194,001 | B2 | 11/2015 | Brenner |
| 9,201,063 | B2 | 12/2015 | Sood et al. |
| 9,273,349 | B2 | 3/2016 | Nguyen et al. |
| 9,290,808 | B2 | 3/2016 | Fodor |
| 9,290,809 | B2 | 3/2016 | Fodor |
| 9,328,383 | B2 | 5/2016 | Van Eijk |
| 9,334,536 | B2 | 5/2016 | Van Eijk |
| 9,371,563 | B2 | 6/2016 | Geiss et al. |
| 9,371,598 | B2 | 6/2016 | Chee |
| 9,376,716 | B2 | 6/2016 | Van Eijk |
| 9,376,717 | B2 | 6/2016 | Gao et al. |
| 9,376,719 | B2 | 6/2016 | Van Eijk |
| 9,416,409 | B2 | 8/2016 | Hayden |
| 9,447,459 | B2 | 9/2016 | Van Eijk |
| 9,453,256 | B2 | 9/2016 | Van Eijk |
| 9,493,820 | B2 | 11/2016 | Van Eijk |
| 9,506,061 | B2 | 11/2016 | Brown |
| 9,512,422 | B2 | 12/2016 | Barnard et al. |
| 9,574,230 | B2 | 2/2017 | Van Eijk |
| 9,593,365 | B2 | 3/2017 | Frisen et al. |
| 9,598,728 | B2 | 3/2017 | Barany et al. |
| 9,624,538 | B2 | 4/2017 | Church et al. |
| 9,644,204 | B2 | 5/2017 | Hindson et al. |
| 9,657,335 | B2 | 5/2017 | Van Eijk |
| 9,670,542 | B2 | 6/2017 | Van Eijk |
| 9,694,361 | B2 | 7/2017 | Bharadwaj |
| 9,702,004 | B2 | 7/2017 | Van Eijk |
| 9,714,446 | B2 | 7/2017 | Webster et al. |
| 9,714,937 | B2 | 7/2017 | Dunaway |
| 9,727,810 | B2 | 8/2017 | Fodor et al. |
| 9,745,627 | B2 | 8/2017 | Van Eijk |
| 9,777,324 | B2 | 10/2017 | Van Eijk |
| 9,783,841 | B2 | 10/2017 | Nolan et al. |
| 9,816,134 | B2 | 11/2017 | Namsaraev |
| 9,834,814 | B2 | 12/2017 | Peter et al. |
| 9,850,536 | B2 | 12/2017 | Oliphant et al. |
| 9,856,521 | B2 | 1/2018 | Stevens et al. |
| 9,868,979 | B2 | 1/2018 | Chee et al. |
| 9,879,313 | B2 | 1/2018 | Chee et al. |
| 9,896,721 | B2 | 2/2018 | Van Eijk |
| 9,898,576 | B2 | 2/2018 | Van Eijk |
| 9,898,577 | B2 | 2/2018 | Van Eijk |
| 9,902,991 | B2 | 2/2018 | Sinicropi et al. |
| 9,909,167 | B2 | 3/2018 | Samusik et al. |
| 9,938,566 | B2 | 4/2018 | Shepard et al. |
| 9,957,550 | B2 | 5/2018 | Yeakley et al. |
| 10,002,316 | B2 | 6/2018 | Fodor et al. |
| 10,023,907 | B2 | 7/2018 | Van Eijk |
| 10,030,261 | B2 | 7/2018 | Frisen et al. |
| 10,035,992 | B2 | 7/2018 | Gloeckner et al. |
| 10,041,949 | B2 | 8/2018 | Bendall et al. |
| 10,059,989 | B2 | 8/2018 | Giresi et al. |
| 10,059,990 | B2 | 8/2018 | Boyden et al. |

(56) References Cited

U.S. PATENT DOCUMENTS

| | | |
|---|---|---|
| 10,095,832 B2 | 10/2018 | Van Eijk |
| 10,144,966 B2 | 12/2018 | Cantor |
| 10,208,982 B2 | 2/2019 | Bannish et al. |
| 10,227,639 B2 | 3/2019 | Levner et al. |
| 10,273,541 B2 | 4/2019 | Hindson et al. |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,008,607 B2 | 5/2021 | Chee |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,479,809 B2 | 10/2022 | Frisen et al. |
| 11,479,810 B1 | 10/2022 | Chee |
| 11,492,612 B1 | 11/2022 | Dadhwal |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 | 12/2022 | Schnall-Levin et al. |
| 11,519,138 B2 | 12/2022 | Meier et al. |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,611,626 B1 | 5/2023 | Katiraee et al. |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 11,835,462 B2 | 12/2023 | Bava |
| 11,840,687 B2 | 12/2023 | Gallant et al. |
| 11,840,724 B2 | 12/2023 | Chew et al. |
| 2001/0055764 A1 | 12/2001 | Empendocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0211489 A1 | 11/2003 | Shen et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0260653 A1 | 11/2005 | LaBaer |

(56) References Cited

U.S. PATENT DOCUMENTS

| | | |
|---|---|---|
| 2005/0266417 A1 | 12/2005 | Barany et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Illumina |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |
| 2013/0005594 A1 | 1/2013 | Terbrueggen et al. |
| 2013/0005600 A1 | 1/2013 | Olek |
| 2013/0023433 A1 | 1/2013 | Luo et al. |
| 2013/0035239 A1 | 2/2013 | Kong et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378350 A1 | 12/2014 | Hindson et al. |
| 2015/0000854 A1 | 1/2015 | Gann-Fetter et al. |
| 2015/0292988 A1 | 10/2015 | Bharadwaj et al. |
| 2015/0344942 A1 | 12/2015 | Frisen et al. |
| 2016/0019337 A1 | 1/2016 | Roberts et al. |
| 2016/0024576 A1 | 1/2016 | Chee |
| 2016/0041159 A1 | 2/2016 | Labaer et al. |
| 2016/0060687 A1 | 3/2016 | Zhu et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0201125 A1 | 7/2016 | Samuels et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0283860 A1 | 4/2017 | Kool et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0080019 A1 | 3/2018 | Blainey et al. |
| 2018/0094316 A1 | 4/2018 | Oliphant et al. |
| 2018/0112261 A1 | 4/2018 | Van Driel et al. |
| 2018/0127817 A1 | 5/2018 | Borchert et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0237864 A1 | 8/2018 | Imler et al. |
| 2018/0245142 A1 | 8/2018 | So et al. |

(56) References Cited

U.S. PATENT DOCUMENTS

| | | |
|---|---|---|
| 2018/0247017 A1 | 8/2018 | van Eijk et al. |
| 2018/0291427 A1 | 10/2018 | Edelman |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2019/0055594 A1 | 2/2019 | Samusik et al. |
| 2019/0064173 A1 | 2/2019 | Bharadwaj et al. |
| 2019/0071656 A1 | 3/2019 | Chang et al. |
| 2019/0085383 A1 | 3/2019 | Church et al. |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0330617 A1 | 10/2019 | Church et al. |
| 2019/0338353 A1 | 11/2019 | Belgrader et al. |
| 2019/0360034 A1 | 11/2019 | Zhou et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0173985 A1 | 6/2020 | Dong et al. |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava et al. |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |

(56) References Cited

U.S. PATENT DOCUMENTS

| | | |
|---|---|---|
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 108949924 | 12/2018 |
| EP | 1782737 | 5/2007 |
| EP | 1910562 | 4/2008 |
| EP | 1923471 | 5/2008 |
| EP | 2002017 | 12/2008 |
| EP | 2292788 | 3/2011 |
| EP | 2302070 | 3/2011 |
| EP | 2881465 | 6/2015 |
| EP | 3013984 | 5/2016 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 2000/17390 | 3/2000 |
| WO | WO 2001/06012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/090415 | 11/2001 |
| WO | WO 2001/096608 | 12/2001 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2009/032167 | 3/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2011/008502 | 1/2011 |
| WO | WO 2011/062933 | 5/2011 |
| WO | WO 2011/068088 | 6/2011 |

(56) References Cited

FOREIGN PATENT DOCUMENTS

| | | |
|---|---|---|
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/144713 | 9/2014 |
| WO | WO 2014/152397 | 9/2014 |
| WO | WO 2014/210223 | 12/2014 |
| WO | WO 2014/210225 | 12/2014 |
| WO | WO 2014/210353 | 12/2014 |
| WO | WO 2015/031691 | 3/2015 |
| WO | WO 2015/161173 | 10/2015 |
| WO | WO 2016/077763 | 5/2016 |
| WO | WO 2016/138496 | 9/2016 |
| WO | WO 2016/138500 | 9/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/075293 | 5/2017 |
| WO | WO 2017/096158 | 7/2017 |
| WO | WO 2017/143155 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2019/165318 | 8/2018 |
| WO | WO 2018/175779 | 9/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/206285 | 10/2020 |
| WO | WO 2020/219901 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/091611 | 5/2021 |
| WO | WO 2021/092433 | 5/2021 |
| WO | WO 2021/097255 | 5/2021 |
| WO | WO 2021/116715 | 6/2021 |
| WO | WO 2021/119320 | 6/2021 |
| WO | WO 2021/133842 | 7/2021 |
| WO | WO 2021/133845 | 7/2021 |
| WO | WO 2021/133849 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/140028 | 6/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/076345 | 5/2023 |
| WO | WO 2023/086880 | 5/2023 |
| WO | WO 2023/102118 | 6/2023 |
| WO | WO 2023/150098 | 8/2023 |
| WO | WO 2023/150163 | 8/2023 |
| WO | WO 2023/150171 | 8/2023 |
| WO | WO 2023/225519 | 11/2023 |

OTHER PUBLICATIONS

U.S. Appl. No. 17/707,189, filed Mar. 29, 2022, Chell et al.

Dalma-Weiszhausz et al., "The Affymetrix GeneChip platform: an overview," Methods Enzymol., 2006, 410:3-28.

Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.

Lahiani et al., "Enabling Histopathological Annotations on Immunofluorescent Images through Virtualization of Hematoxylin and Eosin," J Pathol Inform., Feb. 2018, 9:1, 8 pages.

(56) References Cited

OTHER PUBLICATIONS

Lou et al., "A review of room temperature storage of biospecimen tissue and nucleic acids for anatomic pathology laboratories and biorepositories," Clin Biochem., Mar. 2014, 47(4-5):267-73.
Lykidis et al., "Novel zinc-based fixative for high quality DNA, RNA and protein analysis," Nucleic Acids Res., Jun. 2007, 35(12):e85, 10 pages.
Miller et al., "Chapter 11—Solid and Suspension Microarrays for Microbial Diagnostics," Methods in Microbiology, 2015, 42:395-431.
Nadji et al., "Immunohistochemistry of tissue prepared by a molecular-friendly fixation and processing system," Appl Immunohistochem Mol Morphol., Sep. 2005, 13(3):277-82.
Passow et al., "RNAlater and flash freezing storage methods nonrandomly influence observed gene expression in RNAseq experiments," bioRxiv, Jul. 2018, 28 pages.
Porreca et al., "Polony DNA sequencing," Curr Protoc Mol Biol., Nov. 2006, Chapter 7, Unit 7.8, pp. 7.8.1-7.8.22.
Vickovic et al., "SM-Omics: An automated Platform for High-Throughput Spatial Multi-Omics," bioRxiv, Oct. 2020, 40 pages.
Wohnhaas et al., "DMSO cryopreservation is the method of choice to preserve cells for droplet-based single-cell RNA sequencing," Scientific Reports, Jul. 2019, 9(1):10699, 14 pages.
Fu et al., "Repeat subtraction-mediated sequence capture from a complex genome," Plant J., Jun. 2010, 62(5):898-909.
Ganguli et al., "Pixelated spatial gene expression analysis from tissue," Nat Commun., Jan. 2018, 9(1):202, 9 pages.
Hahnke et al., "Striptease on glass: validation of an improved stripping procedure for in situ microarrays," J Biotechnol., Jan. 2007, 128(1):1-13.
Hu et al., "High reproducibility using sodium hydroxide-stripped long oligonucleotide DNA microarrays," Biotechniques, Jan. 2005, 38(1):121-4.
Lee et al., "Improving the efficiency of genomic loci capture using oligonucleotide arrays for high throughput resequencing," BMC Genomics, Dec. 2009, 10:646, 12 pages.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
U.S. Appl. No. 60/416,118, filed Oct. 3, 2002, Fan et al.
U.S. Appl. No. 61/267,363, filed Dec. 7, 2009, Fan et al.
[No Author Listed], "Chromium Next GEM Single Cell 3' Reagent Kits v3.1," User Guide, Document No. CG000204, 10x Genomics, Nov. 2019, 58 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 70 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwdl9It/e54d99fb08a8f1500aba503005a04a56/CG000238_VisiumSpatialTissueOptimizationUserGuide_RevD.pdf>, 43 pages.

Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Andresen et al., "Helicase-dependent amplification: use in OnChip amplification and potential for point-of-care diagnostics," Expert Rev Mol Diagn., Oct. 2009, 9(7):645-650.
Archer et al., "Selective and flexible depletion of problematic sequences from RNA-seq libraries at the cDNA stage," BMC Genomics, May 2014, 15(1):401, 9 pages.
Armani et al, "2D-PCR: a method of mapping DNA in tissue sections," Lab Chip, 2009, 9(24):3526-34.
Atkinson et al., "An Updated Protocol for High Throughput Plant Tissue Sectioning, " Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription, " Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research, " Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Birney et al., "Identification and analysis of functional elements in 1% of the human genome by the Encode pilot project," Nature, 2007, 447(7146):799-816.
Blanchard et al., "High-density oligonucleotide arrays," Biosensors & Bioelectronics, 1996, 11(6-7):687-690.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.

(56) References Cited

OTHER PUBLICATIONS

Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burton et al., "Coverslip Mounted-Immersion Cycled in Situ RT-PCR for the Localization of mRNA in Tissue Sections," Biotechniques, 1998, 24(1):92-100.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes," Biosensors and Bioelectronics, 2008, 23(12):1878-1882.
Chen et al., "Expansion microscopy," Science, 2015, 347(6221):543-548.
Chen et al., "Nanoscale imaging of RNA with expansion microscopy," Nat Methods, Aug. 2016, 13(8):679-84.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "Spatially resolved, highly multiplexed RNA profiling in single cells," Science, 2015, 348(6233):aaa6090, 21 pages.
Chen et al., "μCB-seq: microfluidic cell barcoding and sequencing for high-resolution imaging and sequencing of single cells," Lab Chip, Nov. 2020, 20(21):3899-3913.
Chrisey et al., "Covalent attachment of synthetic DNA to self-assembled monolayer films," Nucleic Acids Res., Aug. 1996, 24(15):3031-9.
Constantine et al., "Use of genechip high-density oligonucleotide arrays for gene expression monitoring," Life Sceience News, Amersham Life Science, 1998, pp. 11-14.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cujec et al., "Selection of v-abl tyrosine kinase substrate sequences from randomized peptide and cellular proteomic libraries using mRNA display," Chemistry and Biology, 2002, 9(2):253-264.
Dahl et al., "Circle-to-circle amplification for precise and sensitive DNA analysis," Proc. Natl. Acad. Sci., 2004, 101(13):4548-4553.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by nanopore analysis," Acc Chem Res., Oct. 2002, 35(10):817-25.

Dean et al., "Comprehensive human genome amplification using multiple displacement amplification," Proc Natl. Acad. Sci. USA, 2002, 99(8):5261-66.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Continuous Polony Gels for Tissue Mapping with High Resolution and RNA Capture Efficiency," bioRxiv, 2021, 20 pages.
Fullwood et al., "Next-generation DNA sequencing of paired-end tags (PET) for transcriptome and genome analyses," Genome Res., 2009, 19(4):521-532.
Gao et al., "Q&A: Expansion microscopy", BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goryshin et al., "Tn5 in vitro transposition," J Biol Chem., Mar. 1998, 273(13):7367-74.

(56) References Cited

OTHER PUBLICATIONS

Gracia Villacampa et al., "Genome-wide Spatial Expression Profiling in FFPE Tissues," bioRxiv, 2020, pp. 38 pages.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hejatko et al., "In situ hybridization technique for mRNA detection in whole mount *Arabidopsis* samples," Nature Protocols, 2006, 1(4):1939-1946.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Kozlov et al., "A highly scalable peptide-based assay system for proteomics," PLoS One, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches, " Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lampe et al., "A purified mariner transposase is sufficient to mediate transposition in vitro," Embo J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Leriche et al., "Cleavable linkers in chemical biology," Bioorganic & Medicinal Chemistry, 2012, 20:571-582.
Li et al., "A photocleavable fluorescent nucleotide for DNA sequencing and analysis," Proc. Natl. Acad. Sci., 2003, 100(2):414-419.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Lizardi et al., "Mutation detection and single-molecule counting using isothermal rolling-circle amplification," Nat. Genet., 1998, 19(3):225-232.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.

(56) References Cited

OTHER PUBLICATIONS

Lundin et al., "Increased throughput by parallelization of library preparation for massive sequencing," PLoS One, Apr. 2010, 5(4):e10029, 7 pages.

Lyck et al., "Immunohistochemical markers for quantitative studies of neurons and glia in human neocortex," J Histochem Cytochem, 2008, 56(3):201-21.

MacIntyre, "Unmasking antigens for immunohistochemistry.," Br J Biomed Sci., 2001, 58(3):190-6.

Marx, "Method of the Year: spatially resolved transcriptomics," Nature Methods, 2021, 18(1):9-14.

McCloskey et al., "Encoding PCR products with batch-stamps and barcodes," Biochem. Genet., 2007, 45(11-12):761-767.

Meers et al., "Improved CUT&RUN chromatin profiling tools," Elife, Jun. 2019, 8:e46314, 16 pages.

Merritt et al., "Multiplex digital spatial profilin gof proteins and RNA in fixed tissue," Nat Biotechnol, May 2020, 38(5):586-599.

Metzker, "Sequencing technologies—the next generation," Nature Reviews Genetics, 2010, 11(1):31-46.

Miele et al., "Mapping cis- and trans- chromatin interaction networks using chromosome conformation capture (3C)," Methods Mol Biol., 2009, 464:105-21.

Miller et al., "Basic concepts of microarrays and potential applications in clinical microbiology," Clinical Microbiology Reviews, 2009, 22(4):611-633.

Mishra et al., "Three-dimensional genome architecture and emerging technologies: looping in disease," Genome Medicine, 2017, 9(1):87, 14 pages.

Mitra et al., "Digital genotyping and haplotyping with polymerase colonies," Proc. Natl. Acad. Sci. USA, May 2003, 100(10):5926-5931.

Mizusawa et al., "A bacteriophage lambda vector for cloning with BamHI and Sau3A," Gene, 1982, 20(3):317-322.

Motea et al., "Terminal deoxynucleotidyl transferase: the story of a misguided DNA polymerase," Biochim Biophys Acta., May 2010, 1804(5):1151-66.

Nandakumar et al., "How an RNA Ligase Discriminates RNA versus DNA Damage," Molecular Cell, 2004, 16:211-221.

Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.

Ng et al., "Gene identification signature (GIS) analysis for transcriptome characterization and genome annotation," Nature Methods, 2005, 2(2):105-111.

Nichols et al., "RNA Ligases," Curr Protoc Mol Biol., Oct. 2008, 84(1):3.15.1-3.15.4.

Nikiforov et al., "The use of 96-well polystyrene plates for DNA hybridization-based assays: an evaluation of different approaches to oligonucleotide immobilization," Anal Biochem, May 1995, 227(1):201-9.

Niklas et al., "Selective permeabilization for the high-throughput measurement of compartmented enzyme activities in mammalian cells," Anal Biochem, Sep. 2011, 416(2):218-27.

Nowak et al., "Entering the Postgenome Era," Science, 1995, 270(5235):368-71.

Ohtsubo et al., "Bacterial insertion sequences," Curr Top Microbiol Immunol., 1996, 204:1-26.

Pandey et al., "Inhibition of terminal deoxynucleotidyl transferase by adenine dinucleotides. Unique inhibitory action of Ap5A, " FEBS Lett., Mar. 1987, 213(1):204-8.

Park et al., "Single cell trapping in larger microwells capable of supporting cell spreading and proliferation," Microfluid Nanofluid, 2010, 8:263-268.

Pemov et al., "DNA analysis with multiplex microarray-enhanced PCR," Nucl. Acids Res., Jan. 2005, 33(2):e11, 9 pages.

Perler et al., "Intervening sequences in an Archaea DNA polymerase gen," Proc Natl Acad Sci USA, Jun. 1992, 89(12):5577-5581.

Petterson et al., "Generations of sequencing technologies," Genomics, 2009, 93(2):105-111.

Picelli et al., "Tn5 transposase and tagmentation procedures for massively scaled sequencing projects," Genome Res., Dec. 2014, 24(12):2033-40.

Pipenburg et al., "DNA detection using recombination proteins," PLOS Biol., Jul. 2006, 4(7):e204, 7 pages.

Plasterk, "The Tc1/mariner transposon family," Curr Top Microbiol Immunol., 1996, 204:125-43.

Polsky-Cynkin et al., "Use of DNA immobilized on plastic and agarose supports to detect DNA by sandwich hybridization," Clin. Chem., 1985, 31(9):1438-1443.

U.S. Appl. No. 61/267,363, filed Dec. 7, 2009, 33 pages.

Raab et al., "Human tRNA genes function as chromatin insulators," EMBO J., Jan. 2012, 31(2):330-50.

Ranki et al., "Sandwich hybridization as a convenient method for the detection of nucleic acids in crude samples," Gene, 1983, 21(1-2):77-85.

Reinartz et al., "Massively parallel signature sequencing (MPSS) as a tool for in-depth quantitative gene expression profiling in all organisms," Brief Funct Genomic Proteomic, Feb. 2002, 1(1):95-104.

Reznikoff, "Tn5 as a model for understanding DNA transposition," Mol Microbiol., Mar. 2003, 47(5):1199-206.

Rodriques et al., "Slide-seq: A scalable technology for measuring genome-wide expression at high spatial resolution," Science, 2019, 363(6434):1463-1467.

Ronaghi et al., "A sequencing method based on real-time pyrophosphate," Science, Jul. 1998, 281(5375):363-365.

Ronaghi et al., "Real-time DNA sequencing using detection of pyrophosphate release," Analytical Biochemistry, Nov. 1996, 242(1):84-89.

Ronaghi, "Pyrosequencing sheds light on DNA sequencing," Genome Res, Jan. 2001, 11(1):3-11.

Roy et al., "Assessing long-distance RNA sequence connectivity via RNA-templated DNA-DNA ligation," eLife, 2015, 4:e03700, 21 pages.

Saxonov et al., "10x Genomics, Mastering Biology to Advance Human Health," PowerPoint, 10x, 2020, 41 pages.

Schena et al., "Quantitative monitoring of gene expression patterns with a complementary DNA microarray," Science, Oct. 1995, 270(5235):467-470.

Shalon et al., "A DNA microarray system for analyzing complex DNA samples using two-color fluorescent probe hybridization," Genome Res., Jul. 1996, 6(7):639-45.

Shelbourne et al., "Fast copper-free click DNA ligation by the ring-strain promoted alkyne-azide cycloaddition reaction," Chem. Commun., 2011, 47(22):6257-6259.

Shendure et al., "Accurate multiplex polony sequencing of an evolved bacterial genome," Science, 2005, 309(5741):1728-1732.

Simonis et al., "Nuclear organization of active and inactive chromatin domains uncovered by chromosome conformation capture-on-chip (4C)," Nat Genet., Nov. 2006, 38(11):1348-54.

Skene et al., "An efficient targeted nuclease strategy for high-resolution mapping of DNA binding sites," Elife, Jan. 2017, 6:e21856, 35 pages.

Spitale et al., "Structural imprints in vivo decode RNA regulatory mechanisms," Nature, 2015, 519(7544):486-90.

Stahl et al., "Visualization and analysis of gene expression in tissue sections by spatial transcriptomics," Science, Jun. 2016, 353(6294):78-82.

Stahl et al., "Visualization and analysis of gene expression in tissue sections by spatial transcriptomics," Supplementary Materials, Science, Jul. 2016, 353(6294):78-82, 41 pages.

Stimpson et al., "Real-time detection of DNA hybridization and melting on oligonucleotide arrays by using optical wave guides, " Proc Natl Acad Sci USA, Jul. 1995, 92(14):6379-83.

Stoddart et al., "Single-nucleotide discrimination in immobilized DNA oligonucleotides with a biological nanopore," PNAS USA., May 2009, 106(19):7702-7707.

Strell et al., "Placing RNA in context and space—methods for spatially resolved transcriptomics," The FEBS Journal, 2019, 286(8):1468-1481.

(56) References Cited

OTHER PUBLICATIONS

Stroh et al., "Quantum dots spectrally distinguish multiple species within the tumor milieu in vivo," Nat Med., Jun. 2005, 11(6):678-82.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Trejo et al., "Extraction-free whole transcriptome gene expression analysis of FFPE sections and histology-directed subareas of tissue, " PLoS One, Feb. 2019, 14(2):e0212031, 22 pages.
Twyman et al., "Techniques Patents for SNP Genotyping," Pharmacogenomics, Jan. 2003, 4(1):67-79.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Velculescu et al., "Serial analysis of gene expression," Science, Oct. 1995, 270(5235):484-7.
Vickovic et al., "High-definition spatial transcriptomics for in situ tissue profiling," Nature Methods, 2019, 9 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis, " BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems, " RSC Adv., 2017, 7:29966-29984.
Wang et al., "High-fidelity mRNA amplification for gene profiling," Nature Biotechnology, Apr. 2000, 18(4):457-459.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wilson et al., "New transposon delivery plasmids for insertional mutagenesis in Bacillus anthracis," J Microbiol Methods, Dec. 2007, 71(3):332-5.
Wolf et al., "Rapid hybridization kinetics of DNA attached to submicron latex particles," Nucleic Acids Res, 1987, 15(7):2911-2926.

Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Yeakley et al, "Profiling alternative splicing on fiber-optic arrays," Nature biotechnology, 2002, 20:353-358.
Yeakley et al., "A trichostatin A expression signature identified by TempO-Seq targeted whole transcriptome profiling," PLoS One, May 2017, 12(5):e0178302, 22 pages.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zhang et al., "Archaeal RNA ligase from thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a Smart approach for full-length cDNA library construction," Biotechniques, Apr. 2001, 30(4):892-897.
Aran et al., "xCell: digitally portraying the tissue cellular heterogeneity landscape," Genome Biol., Nov. 2017, 18(1):220, 14 pages.
Plongthongkum et al., "Advances in the profiling of DNA modifications: cytosine methylation and beyond," Nature Reviews Genetics, Aug. 2014, 15(10):647-661.
Salmén et al., "Barcoded solid-phase RNA capture for Spatial Transcriptomics profiling in mammalian tissue sections," Nature Protocols, Oct. 2018, 13(11):2501-2534.
Hayes et al., "Electrophoresis of proteins and nucleic acids: I-Theory," BMJ, Sep. 1989, 299(6703):843-6.
Grokhovsky, "Specificity of DNA cleavage by ultrasound," Molecular Biology, 2006, 40(2):276-283.
Schweitzer et al., "Multiplexed protein profiling on microarrays by rolling-circle amplification," Nature Biotechnology, Apr. 2002, 20(4):359-365.
Asp et al., "Spatially Resolved Transcriptomes-Next Generation Tools for Tissue Exploration," Bioessays, Oct. 2020, 42(10):e1900221, 16 pages.
Balakrishnan et al., "Flap endonuclease 1," Annu Rev Biochem., Jun. 2013, 82:119-138.
Bergenståhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Blair et al., "Microarray temperature optimization using hybridization kinetics," Methods Mol Biol., 2009, 529:171-96.
Bolotin et al., "MiXCR: software for comprehensive adaptive immunity profiling, " Nat Methods., May 2015, 12(5):380-1.

(56) References Cited

OTHER PUBLICATIONS

Chen et al., "Parallel single nucleotide polymorphism genotyping by surface invasive cleavage with universal detection," Anal Chem., Apr. 2005, 77(8):2400-5.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Ciaccio et al., "Systems analysis of EGF receptor signaling dynamics with microwestern arrays," Nat Methods, Feb. 2010, 7(2):148-55.
Gerard et al., "Excess dNTPs minimize RNA hydrolysis during reverse transcription," Biotechniques, Nov. 2002, 33(5):984, 986, 988, 990.
Hessner et al., "Genotyping of factor V G1691A (Leiden) without the use of PCR by invasive cleavage of oligonucleotide probes," Clin Chem., Aug. 2000, 46(8 Pt 1):1051-6.
Hoffman et al., "Formaldehyde crosslinking: a tool for the study of chromatin complexes," J Biol Chem., Oct. 2015, 290(44):26404-11.
Hughes et al., "Microfluidic Western blotting," PNAS, Dec. 2012, 109(52):21450-21455.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by chlorella virus DNA ligase and a novel iLock assay with improved direct RNA detection accuracy," Nucleic Acids Research, Oct. 2017, 45(18):e161, 9 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Nilsson et al., "RNA-templated DNA ligation for transcript analysis," Nucleic Acids Res., Jan. 2001, 29(2):578-81.
Olivier, "The Invader assay for SNP genotyping," Mutat. Res., Jun. 2005, 573(1-2):103-110.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perocchi et al., "Antisense artifacts in transcriptome microarray experiments are resolved by actinomycin D," Nucleic Acids Res., 2007, 35(19):e128, 7 pages.
Picelli et al., "Full-length RNA-seq from single cells using Smart-seq2," Nat Protoc., Jan. 2014, 9(1):171-81.
Schouten et al., "Relative quantification of 40 nucleic acid sequences by multiplex ligation-dependent probe amplification," Nucleic Acids Res., Jun. 2002, 30(12):e57, 13 pages.
Singh et al., "High-throughput targeted long-read single cell sequencing reveals the clonal and transcriptional landscape of lymphocytes," Nat Commun., Jul. 2019, 10(1):3120, 13 pages.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Sutherland et al., "Utility of formaldehyde cross-linking and mass spectrometry in the study of protein-protein interactions," J. Mass Spectrom., Jun. 2008, 43(6):699-715.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.

Tu et al., "TCR sequencing paired with massively parallel 3' RNA-seq reveals clonotypic T cell signatures," Nature Immunology, Dec. 2019, 20(12):1692-1699.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Wu et al., "RollFISH achieves robust quantification of single-molecule RNA biomarkers in paraffin-embedded tumor tissue samples, " Commun Biol., Nov. 2018, 1:209, 8 pages.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Bibikova et al., "Quantitative gene expression profiling in formalin-fixed paraffin-embedded tissues using universal bead arrays," The American Journal of Pathology, Nov. 1, 2004, 165(5):1799-1807.
Choi et al., "Multiplexed detection of mRNA using porosity-tuned hydrogel microparticles," Analytical chemistry, Sep. 28, 2012, 84(21):9370-9378.
Fan et al., "A versatile assay for high-throughput gene expression profiling on universal array matrices, " Genome Research, May 1, 2004, 14(5):878-885.
Alam, "Proximity Ligation Assay (PLA)," Curr Protoc Immunol., Nov. 2018, 123(1):e58, 8 pages.
Li et al., "An activity-dependent proximity ligation platform for spatially resolved quantification of active enzymes in single cells," Nat Commun, Nov. 2017, 8(1):1775, 12 pages.
Ristic et al., "Detection of Protein-Protein Interactions and Post-translational Modifications Using the Proximity Ligation Assay: Application to the Study of the SUMO Pathway, " Methods Mol. Biol., 2016, 1449:279-90.
Wang et al., "Imaging-based pooled CRISPR screening reveals regulators of lncRNA localization," Proc Natl Acad Sci USA, May 2019, 116(22):10842-10851.
Wiedmann et al., "Ligase chain reaction (LCR)—overview and applications," PCR Methods Appl., Feb. 1994, 3(4):S51-64.
Appella, "Non-natural nucleic acids for synthetic biology," Current Opinion in Chemical Biology, Dec. 2009, 13(5-6): 687-696.
Bunt et al., "FRET from single to multiplexed signaling events," Biophys Rev. Apr. 2017, 9(2): 119-129.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Ma et al., "Isothermal amplification method for next-generation sequencing," PNAS, Aug. 12, 2013, 110(35):14320-14323.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Niedringhaus et al., "Landscape of next-generation sequencing technologies," Anal Chem., Jun. 2011, 83(12):4327-41.
Qiu et al., "Combination probes with intercalating anchors and proximal fluorophores for DNA and RNA detection," Nucleic Acids Research, Sep. 2016, 44(17):e138, 12 pages.
Zhao et al., "Isothermal Amplification of Nucleic Acids," Chemical Reviews, Nov. 2015, 115(22):12491-12545.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
[No Author Listed], "Chromium Next GEM Single Cell 3' Reagent Kits v3.1 (Dual Index)—User Guide," 10x Genomics, Mar. 2021, Document No. CG000315, 61 pages.

(56) References Cited

OTHER PUBLICATIONS

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/SUJrN0cH17rEk0UXwdl9It/e54d99fb08a8f1500aba503005a04a56/CG000238_VisiumSpatialTissueOptimizationUserGuide_RevD.pdf>, 43 pages.

10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.

Blanco et al., "A practical approach to FRET-based PNA fluorescence in situ hybridization," Methods, Dec. 2010, 52(4):343-51.

Czarnik, "Encoding methods for combinatorial chemistry," Curr Opin Chem Biol., Jun. 1997, 1(1):60-6.

MacBeath et al., "Printing proteins as microarrays for high-throughput function determination," Science, Sep. 2000, 289(5485):1760-1763.

Morlan et al., "Selective depletion of rRNA enables whole transcriptome profiling of archival fixed tissue," PLoS One, Aug. 2012, 7(8):e42882, 8 pages.

Pellestor et al., "The peptide nucleic acids (PNAs), powerful tools for molecular genetics and cytogenetics," Eur J Hum Genet., Sep. 2004, 12(9):694-700.

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.

Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.

Cruz et al., "Methylation in cell-free DNA for early cancer detection," Ann Oncol., Jun. 2018, 29(6):1351-1353.

Hamaguchi et al., "Direct reverse transcription-PCR on oligo(dT)-immobilized polypropylene microplates after capturing total mRNA from crude cell lysates," Clin Chem., Nov. 1998, 44(11):2256-63.

Ke et al., "In situ sequencing for RNA analysis in preserved tissue and cells," Nat Methods., Sep. 2013, Supplementary Materials, 29 pages.

Miner et al., "Molecular barcodes detect redundancy and contamination in hairpin-bisulfite PCR," Nucleic Acids Res., Sep. 2004, 32(17):e135, 4 pages.

Wang et al., "Tagmentation-based whole-genome bisulfite sequencing, " Nature Protocols, Oct. 2013, 8(10):2022-2032.

U.S. Appl. No. 63/033,348, filed Jun. 2, 2020, Bent.

Arslan et al., "Engineering of a superhelicase through conformational control (Supplementary Materials)," Science, Apr. 17, 2015, 348(6232):344-347, 18 pages.

Arslan et al., "Engineering of a superhelicase through conformational control," Science, Apr. 17, 2015, 348(6232):344-347.

Baner et al., "Signal amplification of padlock probes by rolling circle replication," Nucleic Acids Res., 1998, 26(22):5073-5078.

Borm et al., "High throughput Human embryo spatial transcriptome mapping by surface transfer of tissue RNA," Abstracts Selected Talks, Single Cell Genomics mtg, (SCG2019), 2019, 1 pages (Abstract Only).

Chen et al., "Efficient in situ barcode sequencing using padlock probe-based BaristaSeq," Nucleic Acids Res., 2018, 46(4): e22, 11 pages.

Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.

Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.

Codeluppi et al., "Spatial organization of the somatosensory cortex revealed by osmFISH, " Nature Methods, Nov. 2018, 15:932-935.

Dean et al., "Rapid Amplification of Plasmid and Phage DNA Using Phi29 DNA Polymerase and Multiply-Primed Rolling Circle Amplification," Genome Research, Jun. 2001, 11:1095-1099.

Eng et al., "Transcriptome-scale super-resolved imaging in tissues by RNA seqFISH+," Nature, Apr. 2019, 568(7751):235-239, 37 pages.

Ergin et al., "Proteomic Analysis of PAXgene-Fixed Tissues," J Proteome Res., 2010, 9(10):5188-96.

Faruqi et al., "High-throughput genotyping of single nucleotide polymorphisms with rolling circle amplification," BMC Genomics, Aug. 2001, 2:4, 10 pages.

Gao et al., "A highly homogeneous expansion microscopy polymer composed of tetrahedron-like monomers," bioRxiv, Oct. 22, 2019, 23 pages (Preprint).

Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.

Goh et al., "Highly Specific Multiplexed RNA Imaging in Tissues With Split-FISH," Nat Methods, Jun. 15, 2020, 17(7):689-693, 21 pages.

Goransson et al., "A single molecule array for digital targeted molecular analyses," Nucleic Acids Res., Nov. 25, 2009, 37(1):e7, 9 pages.

Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.

Liu et al., "High-Spatial-Resolution Multi-Omics Sequencing via Deterministic Barcoding in Tissue," Cell, Nov. 13, 2020, 183(6):1665-1681, 36 pages.

Liu et al., "Spatial transcriptome sequencing of FFPE tissues at cellular level," bioRxiv 788992, Oct. 14, 2020, 39 pages.

Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.

Mignardi et al., "Oligonucleotide gap-fill ligation for mutation detection and sequencing in situ," Nucleic Acids Research, Aug. 3, 2015, 43(22):e151, 12 pages.

Mohsen et al., "The Discovery of Rolling Circle Amplification and Rolling Circle Transcription," Acc Chem Res., Nov. 15, 2016, 49(11):2540-2550, 25 pages.

Nallur et al., "Signal amplification by rolling circle amplification on DNA microarrays," Nucleic Acids Res., Dec. 1, 2001, 29(23):e118, 9 pages.

Raj et al., "Imaging individual mRNA molecules using multiple singly labeled probes," Nature Methods, Oct. 2008, 5(10):877-879, 9 pages.

Schweitzer et al., "Immunoassays with rolling circle DNA amplification: A versatile platform for ultrasensitive antigen detection," Proc. Natl Acad. Sci. USA, May 22, 2000, 97:10113-119.

Takei et al., "Integrated Spatial Genomics Reveals Global Architecture of Single Nuclei," Nature, Jan. 27, 2021, 590(7845):344-350, 53 pages.

Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.

Howell et al., "iFRET: An Improved Fluorescence System for DNA-Melting Analysis," Genome Research, 2002, 12:1401-1407.

Nam et al., "Nanoparticle-Based Bio-Bar Codes for the Ultrasensitive Detection of Proteins," Science, Sep. 26, 2003, 301(5641):1884-1886.

Redmond et al., "Single-cell TCRseq: paired recovery of entire T-cell alpha and beta chain transcripts in T-cell receptors from single-cell RNAseq," Genome Med, 2016, 8:80, 12 pages.

Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.

Belton et al., "Hi-C: A comprehensive technique to capture the conformation of genomes," Methods, Nov. 2012, 58(3):268-276, 16 pages.

(56) References Cited

OTHER PUBLICATIONS

Bentzen et al., "Large-scale detection of antigen-specific T cells using peptide-MHC-I multimers labeled with DNA barcodes," Nat Biotechnol., Oct. 2016, 34(10):1037-1045, 12 pages.

Chen et al. "Arrayed profiling of multiple glycans on whole living cell surfaces." Analytical chemistry, Oct. 15, 2013, 85(22):11153-11158.

Fan et al., "Illumina Universal Bead Arrays," Methods in Enzymology, 2006, 410:57-73.

Hadrup et al., "Parallel detection of antigen-specific T-cell responses by multidimensional encoding of MHC multimers," Nat. Methods., Jul. 2009, 6(7), 520-526.

Hobro et al, "An evaluation of fixation methods: Spatial and compositional cellular changes observed by Raman imaging," Vibrational Spectroscopy, Jul. 2017, 91:31-45.

Landegren et al., "A Ligase-Mediated Gene Detection Technique," Science, 1988, 241(4869):1077-1080.

Mamedov et al., "Preparing unbiased T-cell receptor and antibody cDNA libraries for the deep next generation sequencing profiling," Frontiers in Immunol., Dec. 23, 2013, 4(456):1-10.

Oksuz et al., "Systematic evaluation of chromosome conformation capture assays," Nature Methods, Sep. 2021, 18:1046-1055.

Rohland et al., "Partial uracil-DNA-glycosylase treatment for screening of ancient DNA," Phil. Trans. R. Soc. B, Jan. 19, 2015, 370(1660): Jun. 24, 2013, 11 pages.

Schmidl et al., "ChIPmentation: fast, robust, low-input ChIP-seq for histones and transcription factors," Nature Methods, Oct. 2015, 12:963-965.

Su et al., "Restriction enzyme selection dictates detection range sensitivity in chromatin conformation capture-based variant-to-gene mapping approaches," bioRxiv, Dec. 15, 2020, 22 pages.

Sun et al., "Statistical Analysis of Spatial Expression Pattern for Spatially Resolved Transcriptomic Studies," Nature Methods, Jan. 27, 2020, 17(2): 193-200.

Svensson et al., "SpatialDE: identification of spatially variable genes," Nature Methods, May 2018, 15:343-346, 15 pages.

METHODS OF MAKING GENE EXPRESSION LIBRARIES

CROSS-REFERENCE TO RELATED APPLICATIONS

This application claims priority to U.S. Provisional Patent Application Ser. No. 62/980,867, filed Feb. 24, 2020; the entire contents of which are herein incorporated by reference.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

SUMMARY

This application is based on the discovery of a method of making a spatial 5' gene expression library for spatial analysis of target analytes, including long target analytes e.g., VDJ rearranged T-cell receptors or immunoglobulins.

Provided herein are methods of identifying a location of a target nucleic acid in a permeabilized biological sample, the method comprising: (a) generating a cDNA molecule comprising a sequence that is substantially complementary to the target nucleic acid using a reverse transcription primer comprising (i) a sequence that is substantially complementary to a portion of the target nucleic acid and (ii) a first adaptor sequence, wherein the step of generating the cDNA molecule occurs within the permeabilized biological sample; (b) ligating a second adaptor sequence to a 3' end of the cDNA molecule, wherein the step of ligating is performed within the biological sample; (c) after step (b), releasing the cDNA molecule from the target nucleic acid, such that the cDNA contacts an array, wherein the array comprises an attached capture probe comprising in a 5' to a 3' direction: (i) a spatial barcode and (ii) a capture domain that binds specifically to the second adaptor sequence ligated to the cDNA; (d) after step (c), extending a 3' end of the capture probe using the cDNA as a template; and (e) determining (i) all or a part of the sequence of the target nucleic acid, or a complement thereof, and (ii) all or a part of the sequence of the spatial barcode, or a complement thereof, and using the determined sequences of (i) and (ii) to identify the location of the target nucleic acid in the permeabilized biological sample.

Also provided herein are methods of identifying a location of a target nucleic acid in a permeabilized biological sample, the method comprising: (a) generating a cDNA molecule comprising a sequence that is substantially complementary to the target nucleic acid using a reverse transcription primer comprising (i) a sequence that is substantially complementary to a portion of the target nucleic acid and (ii) a first adaptor sequence, wherein the step of generating the cDNA molecule occurs within the permeabilized biological sample; (b) extending a 3' end of the cDNA molecule to include a second adaptor sequence, wherein the step of extending is performed within the biological sample; (c) releasing the cDNA molecule from the target nucleic acid, such that the cDNA contacts an array, wherein the array comprises an attached capture probe comprising in a 5' to a 3' direction: (i) a spatial barcode and (ii) a capture domain that binds specifically to the second adaptor sequence; (d) extending a 3' end of the capture probe using the cDNA as a template; and (e) determining (i) all or a part of the sequence of the target nucleic acid, or a complement thereof, and (ii) the sequence of the spatial barcode, or a complement thereof, and using the determined sequences of (i) and (ii) to identify the location of the target nucleic acid in the permeabilized biological sample. In some embodiments, step (b) can occur simultaneously with step (a).

In some embodiments of any of the methods described herein, steps (a) through (c) are performed when the biological sample is disposed on the array.

In some embodiments of any of the methods described herein, step (a) is performed when the biological sample is not disposed on the array and step (b) is performed when the biological sample is disposed on the array, and wherein the method further comprises between steps (a) and (b), a step of disposing the biological sample on the array.

In some embodiments of any of the methods described herein, steps (a) and (b) are performed when the biological sample is not disposed on the array, and wherein the method further comprises between steps (b) and (c), a step of disposing the biological sample on the array.

In some embodiments of any of the methods described herein, the sequence that is substantially complementary to a portion of the target nucleic acid present in the reverse transcription primer comprises a poly(T) sequence.

In some embodiments of any of the methods described herein, the sequence that is substantially complementary to a portion of the target nucleic acid present in the reverse transcription primer comprises a random sequence.

In some embodiments of any of the methods described herein, the second adaptor sequence is a template switching oligonucleotide (TSO).

In some embodiments of any of the methods described herein, the array comprises a slide.

In some embodiments of any of the methods described herein, a 5' end of the capture probe is attached to the slide.

In some embodiments of any of the methods described herein, the array is a bead array.

In some embodiments of any of the methods described herein, a 5' end of the capture probe is attached to a bead of the bead array.

In some embodiments of any of the methods described herein, the capture probe further comprises a unique molecular identifier (UMI).

In some embodiments of any of the methods described herein, the UMI is positioned 5' relative to the capture domain in the capture probe.

In some embodiments of any of the methods described herein, the determining in step (e) comprises sequencing (i) all or a part of the sequence of the target nucleic acid, or a complement thereof, and (ii) all or a part of the sequence of the spatial barcode, or a complement thereof.

In some embodiments of any of the methods described herein, the sequencing is high throughput sequencing.

In some embodiments of any of the methods described herein, the sequencing is sequencing by hybridization.

In some embodiments of any of the methods described herein, the target nucleic acid is RNA.

In some embodiments of any of the methods described herein, the RNA is an mRNA.

In some embodiments of any of the methods described herein, the permeabilized biological sample is a permeabilized tissue section.

In some embodiments of any of the methods described herein, the permeabilized tissue section is a permeabilized formalin-fixed and paraffin-embedded (FFPE) tissue section.

Some embodiments of any of the methods described herein further comprises a step of imaging the biological sample.

In some embodiments of any of the methods described herein, the step of imaging is performed prior to step (a).

In some embodiments of any of the methods described herein, the step of imaging is performed between steps (b) and (c).

Some embodiments of any of the methods described herein further comprises, between steps (b) and (c), a step of freezing and thawing the permeabilized biological sample.

Some embodiments of any of the methods described herein further comprises, between steps (b) and (c), a step of sectioning the permeabilized biological sample.

In some embodiments of any of the methods described herein, the step of sectioning the permeabilized biological sample is performed using cryosectioning.

Some embodiments of any of the methods described herein further comprises, prior to step (a), a step of permeabilizing the biological sample.

In some embodiments of any of the methods described herein, the performance of step (a) comprises introducing a reverse transcriptase, dNTPs, and the reverse transcription primer into the permeabilized biological sample.

In some aspects, provided herein are kits comprising: a reverse transcription primer comprising (i) a sequence that is substantially complementary to a portion of the target nucleic acid and (ii) a first adaptor sequence; a reverse transcriptase; and an oligonucleotide comprising a second adaptor sequence or a complement thereof.

In some embodiments of any of the kits provided herein, the kit further comprises a ligase.

In some embodiments of any of the kits provided herein, the reverse transcriptase is a reverse transcriptase with terminal transferase activity.

In some embodiments of any of the kits provided herein, the second adaptor sequence or the complement thereof is a TSO or a complement thereof.

In some embodiments of any of the kits provided herein, the kit further comprises an array, wherein the array comprises an attached capture probe comprising in a 5' to a 3' direction: (i) a spatial barcode and (ii) a capture domain that binds specifically to the second adaptor sequence.

In another aspect, provided herein are nucleic acids comprising, in the 5' to 3' direction: a spatial barcode; a sequence complementary to a second adaptor sequence; a sequence present in a target nucleic acid; and a sequence complementary to a first adaptor sequence.

In another aspect, provided herein are nucleic acids comprising, in the 3' to 5' direction: a complement of a spatial barcode; a second adaptor sequence; a sequence complementary to a sequence present in a target nucleic acid; and a first adaptor sequence.

In some embodiments of any of the nucleic acids provided herein, the second adaptor sequence comprises a TSO.

In some embodiments of any of the nucleic acids provided herein, the second adaptor sequence comprises a complement of a TSO.

In some embodiments of any of the nucleic acids provided herein, the first adaptor sequence is a reverse transcriptase primer.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise. Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

DETAILED DESCRIPTION

Figure 1A:
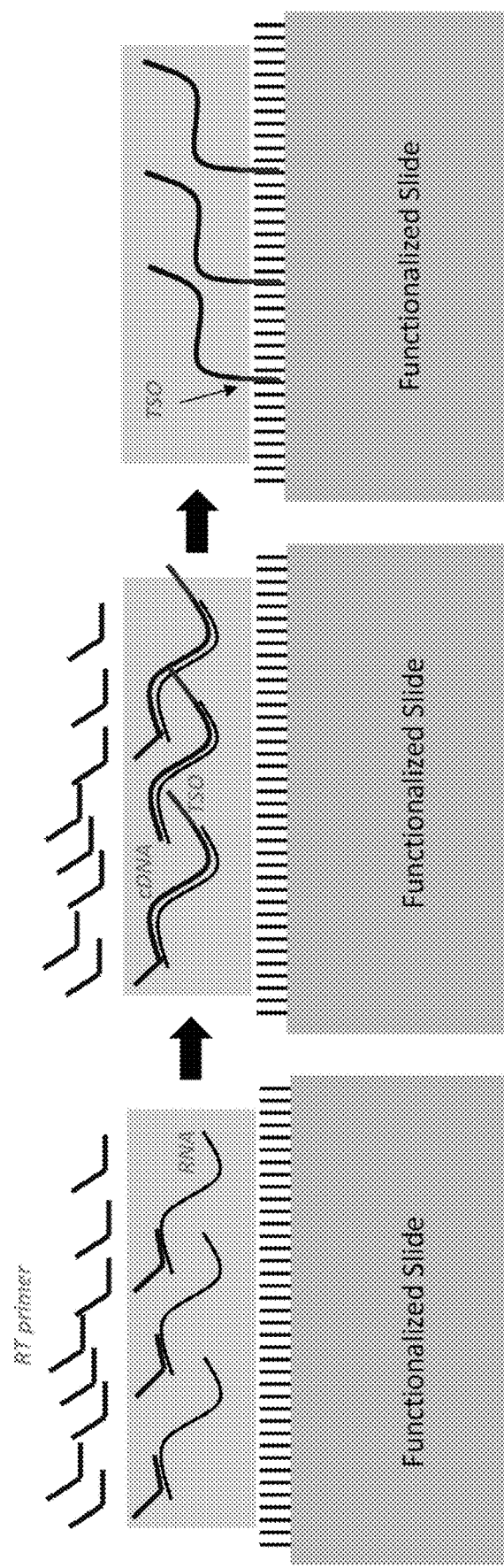
FIG. 1A shows a workflow schematic illustrating exemplary, non-limiting steps for in-situ cDNA synthesis and capturing.

In some cases, spatial analysis methods can be carried out by permeabilizing a biological sample, capturing analytes (e.g., nucleic acids (e.g., mRNA)) or intermediate agents on an array, and performing reverse transcription and sequencing steps to identify the location of one or more analytes from the biological sample. Many capture protocols rely on the use of a poly(A) tail, either natural or introduced. Several challenges can arise from these protocols. For example, there may or may not be biased in the analytes or intermediate agents that are able to migrate from a biological sample to the array. As another example, capture by the poly(A) tail can lead to a 3' bias in gene expression libraries generated from mRNAs due to limitations of some steps of the process. Provided herein are methods that can, in some cases, address one or both of these challenges.

Provided herein are methods of identifying a location of a target nucleic acid in a permeabilized biological sample, the method comprising: (a) generating a cDNA molecule comprising a sequence that is substantially complementary to the target nucleic acid using a reverse transcription primer comprising (i) a sequence that is substantially complementary to a portion of the target nucleic acid and (ii) a first adaptor sequence, wherein the step of generating the cDNA molecule occurs within the permeabilized biological sample; (b) ligating a second adaptor sequence to a 3' end of the cDNA molecule, wherein the step of ligating is performed within the biological sample; (c) after step (b), releasing the cDNA molecule from the target nucleic acid, such that the cDNA contacts an array, wherein the array comprises an attached capture probe comprising in a 5' to a 3' direction: (i) a spatial barcode and (ii) a capture domain that binds specifically to the second adaptor sequence ligated to the cDNA; (d) after step (c), extending a 3' end of the capture probe using the cDNA as a template; and (e) determining (i) all or a part of the sequence of the target nucleic acid, or a complement thereof, and (ii) all or a part of the sequence of the spatial barcode, or a complement thereof, and using the determined sequences of (i) and (ii) to identify the location of the target nucleic acid in the permeabilized biological sample. Non-limiting aspects of these methods are described herein.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture domain can include a sequence that is significantly complementary to an analyte, a complement thereof, or a portion thereof (e.g., a capture domain can include a poly-T sequence). In some embodiments, a capture domain can include a sequence that is significantly complementary to a sequence introduced to the analyte before capture (e.g., a capture domain can include a sequence complementary to a functional domain and/or an adaptor sequence (e.g., a template switching oligonucleotide sequence)). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, genetic material is amplified by reverse transcription polymerase chain reaction (RT-PCR). The desired reverse transcriptase activity can be provided by one or more distinct reverse transcriptase enzymes (i.e., RNA dependent DNA polymerases), suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g., reverse transcriptase, activity of the wild-type sequence. The reverse transcriptase enzyme can be provided as part of a composition that includes other components, e.g., stabilizing components that enhance or improve the activity of the reverse transcriptase enzyme, such as RNase inhibitor(s), inhibitors of DNA-dependent DNA synthesis, e.g., actinomycin D. Many sequence-modified derivative or mutants of reverse transcriptase enzymes, e.g., M-MLV, and compositions including unmodified and modified enzymes are commercially available, e.g., ArrayScript™, MultiScribe™, ThermoScript™, and SuperScript® I, II, III, and IV enzymes.

Certain reverse transcriptase enzymes (e.g., Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g., an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™", or dyes such as "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

A "template switching oligonucleotide" (TSO) is an oligonucleotide that hybridizes to untemplated nucleotides added by a reverse transcriptase (e.g., enzyme with terminal transferase activity) during reverse transcription. In some embodiments, a template switching oligonucleotide hybridizes to untemplated poly(C) nucleotides added by a reverse transcriptase. In some embodiments, the template switching oligonucleotide adds a common 5' sequence to full-length cDNA that is used for cDNA amplification.

In some embodiments, the template switching oligonucleotide adds a common sequence onto the 5' end of the RNA being reverse transcribed. For example, a template switching oligonucleotide can hybridize to untemplated poly(C) nucleotides added onto the end of a cDNA molecule and provide a template for the reverse transcriptase to continue replication to the 5' end of the template switching oligonucleotide, thereby generating full-length cDNA ready for further amplification. In some embodiments, once a full-length cDNA molecule is generated, the template switching oligonucleotide can serve as a primer in a cDNA amplification reaction.

In some embodiments, a template switching oligonucleotide is added before, contemporaneously with, or after a reverse transcription, or other terminal transferase-based reaction. In some embodiments, a template switching oligonucleotide or complement thereof is included in the capture probe. In some embodiments, the TSO, or complement thereof, in the capture probe serves as a capture domain. In certain embodiments, methods of sample analysis using template switching oligonucleotides can involve the generation of nucleic acid products from analytes of the tissue sample, followed by further processing of the nucleic acid products with the template switching oligonucleotide.

Template switching oligonucleotides can include a hybridization region and a template region. The hybridization region can include any sequence capable of hybridizing to the target sequence. In some embodiments, the hybridization region can, e.g., include a series of G bases to complement the overhanging C bases at the 3' end of a cDNA molecule. The series of G bases can include 1 G base, 2 G bases, 3 G bases, 4 G bases, 5 G bases, or more than 5 G bases. The template sequence can include any sequence to be incorporated into the cDNA. In other embodiments, the hybridization region can include at least one base in addition to at least one G base. In other embodiments, the hybridization can include bases that are not a G base. In some embodiments, the template region includes at least 1 (e.g., at least 2, 3, 4, 5 or more) tag sequences and/or functional sequences. In some embodiments, the template region and hybridization region are separated by a spacer.

In some embodiments, the template regions include a barcode sequence. The barcode sequence can act as a spatial barcode and/or as a unique molecular identifier. In some embodiments, the template region can include a functional region, for example a region that can be used for amplification, a region that is complementary to a capture domain on a capture probe, etc. In some embodiments, the template region can include a barcode and/or a unique molecular identifier and/or a functional sequence and/or a capture domain sequence. Template switching oligonucleotides can include deoxyribonucleic acids; ribonucleic acids; modified nucleic acids including 2-aminopurine, 2,6-diaminopurine (2-amino-dA), inverted dT, 5-methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' fluoro bases (e.g., Fluoro C, Fluoro U, Fluoro A, and Fluoro G), or any combination of the foregoing.

In some embodiments, the length of a template switching oligonucleotide can be at least about 1, 2, 10, 20, 50, 75, 100, 150, 200, or 250 nucleotides or longer. In some embodiments, the length of a template switching oligonucleotide can be at most about 2, 10, 20, 50, 100, 150, 200, or 250 nucleotides or longer.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligation products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. patent application Ser. No. 16/951,843. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Spatial 5' Gene Expression Libraries

Provided herein are methods of identifying a location of a target nucleic acid in a permeabilized biological sample, the method comprising: (a) generating a cDNA molecule comprising a sequence that is substantially complementary to the target nucleic acid using a reverse transcription primer comprising (i) a sequence that is substantially complementary to a portion of the target nucleic acid and (ii) a first adaptor sequence, wherein the step of generating the cDNA molecule occurs within the permeabilized biological sample; (b) ligating a second adaptor sequence to a 3' end of the cDNA molecule, wherein the step of ligating is performed within the biological sample; (c) releasing the cDNA molecule from the target nucleic acid, such that the cDNA molecule contacts an array, wherein the array comprises an attached capture probe comprising in a 5' to a 3' direction: (i) a spatial barcode and (ii) a capture domain that binds specifically to the second adaptor sequence ligated to the cDNA; (d) extending a 3' end of the capture probe using the cDNA as a template; and (e) determining (i) all or a part of the sequence of the target nucleic acid, or a complement thereof, and (ii) all or a part of the sequence of the spatial barcode, or a complement thereof, and using the determined sequences of (i) and (ii) to identify the location of the target nucleic acid in the permeabilized biological sample.

Also provided herein are methods of identifying a location of a target nucleic acid in a permeabilized biological sample, the method comprising: (a) generating a cDNA molecule comprising a sequence that is substantially complementary to the target nucleic acid using a reverse transcription primer comprising (i) a sequence that is substantially complementary to a portion of the target nucleic acid and (ii) a first adaptor sequence, wherein the step of generating the cDNA molecule occurs within the permeabilized biological sample; (b) extending a 3' end of the cDNA molecule to include a second adaptor sequence, wherein the step of extending is performed within the biological sample; (c) releasing the cDNA molecule from the target nucleic acid, such that the cDNA contacts an array, wherein the array comprises an attached capture probe comprising in a 5' to a 3' direction: (i) a spatial barcode and (ii) a capture domain that binds specifically to the second adaptor sequence ligated to the cDNA; (d) extending a 3' end of the capture probe using the cDNA as a template; and (e) determining (i) all or a part of the sequence of the target nucleic acid, or a complement thereof, and (ii) all or a part of the sequence of the spatial barcode, or a complement thereof, and using the determined sequences of (i) and (ii) to identify the location of the target nucleic acid in the permeabilized biological sample. In some such embodiments, the method can further comprise hybridizing a template switching oligonucleotide (TSO) to the cDNA molecule. Therefore, in some embodiments, (b) comprises extending a 3' end of the cDNA molecule to include a complement of a TSO. In some cases, the TSO can be added to the sample at the same time as the reverse transcriptase primer.

In some embodiments, steps (a) through (c) are performed when the biological sample is disposed on the array. In some embodiments, step (a) is performed when the biological sample is not disposed on the array and step (b) is performed when the biological sample is disposed on the array, and wherein the method further comprises between steps (a) and (b), a step of disposing the biological sample on the array. In some embodiments, steps (a) and (b) are performed when the biological sample is not disposed on the array, and wherein the method further comprises between steps (b) and (c), a step of disposing the biological sample on the array.

In some embodiments of any of the methods described herein, the biological sample can be any of the exemplary permeabilized biological samples described herein (e.g., a permeabilized tissue sample, e.g., a permeabilized permeabilized tissue section), or any of the same described in, e.g., Section (I)(d) (e.g., (I)(d)(i) and/or (I)(d)(ii)(13)) of WO 2020/176788 and/or U.S. Patent Application Publication No. 2020/0277663. Some embodiments described herein can optionally further include a step of permeabilizing the biological sample (e.g., using any of the exemplary methods and agents for permeabilizing a biological sample described herein). In some embodiments, the target nucleic acid is RNA (e.g., mRNA).

In embodiments, the reverse transcription primer can have a total of about 10 nucleotides to about 250 nucleotides (e.g., about 10 nucleotides to about 225 nucleotides, about 10 nucleotides to about 200 nucleotides, about 10 nucleotides to about 175 nucleotides, about 10 nucleotides to about 150 nucleotides, about 10 nucleotides to about 125 nucleotides, about 10 nucleotides to about 100 nucleotides, about 10 nucleotides to about 80 nucleotides, about 10 nucleotides to about 60 nucleotides, about 10 nucleotides to about 40 nucleotides, about 10 nucleotides to about 20 nucleotides, about 20 nucleotides to about 250 nucleotides, about 20 nucleotides to about 225 nucleotides, about 20 nucleotides to about 200 nucleotides, about 20 nucleotides to about 175 nucleotides, about 20 nucleotides to about 150 nucleotides, about 20 nucleotides to about 125 nucleotides, about 20 nucleotides to about 100 nucleotides, about 20 nucleotides to about 80 nucleotides, about 20 nucleotides to about 60 nucleotides, about 20 nucleotides to about 40 nucleotides, about 40 nucleotides to about 250 nucleotides, about 40 nucleotides to about 225 nucleotides, about 40 nucleotides to about 200 nucleotides, about 40 nucleotides to about 175 nucleotides, about 40 nucleotides to about 150 nucleotides, about 40 nucleotides to about 125 nucleotides, about 40 nucleotides to about 100 nucleotides, about 40 nucleotides to about 80 nucleotides, about 40 nucleotides to about 60 nucleotides, about 60 nucleotides to about 250 nucleotides, about 60 nucleotides to about 225 nucleotides, about 60 nucleotides to about 200 nucleotides, about 60 nucleotides to about 175 nucleotides, about 60 nucleotides to about 150 nucleotides, about 60 nucleotides to about 125 nucleotides, about 60 nucleotides to about 100 nucleotides, about 60 nucleotides to about 80 nucleotides, about 80 nucleotides to about 250 nucleotides, about 80 nucleotides to about 225 nucleotides, about 80 nucleotides to about 200 nucleotides, about 80 nucleotides to about 175 nucleotides, about 80 nucleotides to about 150 nucleotides, about 80 nucleotides to about 125 nucleotides, about 80 nucleotides to about 100 nucleotides, about 100 nucleotides to about 250 nucleotides, about 100 nucleotides to about 225 nucleotides, about 100 nucleotides to about 200 nucleotides, about 100 nucleotides to about 175 nucleotides, about 100 nucleotides to about 150 nucleotides, about 100 nucleotides to about 125 nucleotides, about 125 nucleotides to about 250 nucleotides, about 125 nucleotides to about 225 nucleotides, about 125 nucleotides to about 200 nucleotides, about 125 nucleotides to about 175 nucleotides, about 125 nucleotides to about 150 nucleotides, about 150 nucleotides to about 250 nucleotides, about 150 nucleotides to about 225 nucleotides, about 150 nucleotides to about 200 nucleotides, about 150 nucleotides to about 175 nucleotides, about 175 nucleotides to about 250 nucleotides, about 175 nucleotides to about 225 nucleotides, about 175 nucleotides to about 200 nucleotides, about 200 nucleotides to about 250 nucleotides, about 200 nucleotides to about 225 nucleotides, or about 225 nucleotides to about 250 nucleotides).

In some embodiments of any of the methods described herein, the first adaptor sequence has a total of about 5 nucleotides to about 125 nucleotides (e.g., about 5 nucleotides to about 100 nucleotides, about 5 nucleotides to about 90 nucleotides, about 5 nucleotides to about 80 nucleotides, about 5 nucleotides to about 70 nucleotides, about 5 nucleotides to about 60 nucleotides, about 5 nucleotides to about 50 nucleotides, about 5 nucleotides to about 45 nucleotides, about 5 nucleotides to about 40 nucleotides, about 5 nucleotides to about 35 nucleotides, about 5 nucleotides to about 30 nucleotides, about 5 nucleotides to about 25 nucleotides, about 5 nucleotides to about 20 nucleotides, about 5 nucleotides to about 15 nucleotides, about 5 nucleotides to about 10 nucleotides, about 10 nucleotides to about 125 nucleotides, about 10 nucleotides to about 100 nucleotides, about 10 nucleotides to about 90 nucleotides, about 10 nucleotides to about 80 nucleotides, about 10 nucleotides to about 70 nucleotides, about 10 nucleotides to about 60 nucleotides, about 10 nucleotides to about 50 nucleotides, about 10 nucleotides to about 45 nucleotides, about 10 nucleotides to about 40 nucleotides, about 10 nucleotides to about 35 nucleotides, about 10 nucleotides to about 30 nucleotides, about 10 nucleotides to about 25 nucleotides, about 10 nucleotides to about 20 nucleotides, about 10 nucleotides to about 15 nucleotides, about 20 nucleotides to about 125 nucleotides, about 20 nucleotides to about 100 nucleotides, about 20 nucleotides to about 90 nucleotides, about 20 nucleotides to about 80 nucleotides, about 20 nucleotides to about 70 nucleotides, about 20 nucleotides to about 60 nucleotides, about 20 nucleotides to about 50 nucleotides, about 20 nucleotides to about 45 nucleotides, about 20 nucleotides to about 40 nucleotides, about 20 nucleotides to about 35 nucleotides, about 20 nucleotides to about 30 nucleotides, about 20 nucleotides to about 25 nucleotides, about 30 nucleotides to about 125 nucleotides, about 30 nucleotides to about 100 nucleotides, about 30 nucleotides to about 90 nucleotides, about 30 nucleotides to about 80 nucleotides, about 30 nucleotides to about 70 nucleotides, about 30 nucleotides to about 60 nucleotides, about 30 nucleotides to about 50 nucleotides, about 30 nucleotides to about 45 nucleotides, about 30 nucleotides to about 40 nucleotides, about 30 nucleotides to about 35 nucleotides, about 40 nucleotides to about 125 nucleotides, about 40 nucleotides to about 100 nucleotides, about 40 nucleotides to about 90 nucleotides, about 40 nucleotides to about 80 nucleotides, about 40 nucleotides to about 70 nucleotides, about 40 nucleotides to about 60 nucleotides, about 40 nucleotides to about 50 nucleotides, about 40 nucleotides to about 45 nucleotides, about 50 nucleotides to about 125 nucleotides, about 50 nucleotides to about 100 nucleotides, about 50 nucleotides to about 90 nucleotides, about 50 nucleotides to about 80 nucleotides, about 50 nucleotides to about 70 nucleotides, about 50 nucleotides to about 60 nucleotides, about 60 nucleotides to about 125 nucleotides, about 60 nucleotides to about 100 nucleotides, about 60 nucleotides to about 90 nucleotides, about 60 nucleotides to about 80 nucleotides, about 60 nucleotides to about 70 nucleotides, about 70 nucleotides to about 125 nucleotides, about 70 nucleotides to about 100 nucleotides, about 70 nucleotides to about 90 nucleotides, about 70 nucleotides to about 80 nucleotides, about 80 nucleotides to about 125 nucleotides, about 80 nucleotides to about 100 nucleotides, about 80 nucleotides to about 90 nucleotides, about 90 nucleotides to about 125 nucleotides, about 90 nucleotides to about 100 nucleotides, or about 100 nucleotides to about 125 nucleotides). In some embodiments, the first adaptor sequence can be any predetermined sequence. In some embodiments, the first adaptor sequence does not encode a polypeptide and/or can be non-naturally occurring sequence.

In some embodiments the sequence that is substantially complementary (e.g., at least 80%, at least 85%, at least 90%, at least 95%, at least 99%, or 100% complementary) to a portion of the sequence of the target nucleic acid (that is present in the reverse transcription primer) can have a total of about 10 nucleotides to about 125 nucleotides (or any of the subranges of this range described herein). In some embodiments, the sequence that is substantially complementary to a portion of the sequence of the target nucleic acid can be a random sequence. In some embodiments, the sequence that is substantially complementary to a portion of the sequence of the target nucleic acid can include a poly(T) oligonucleotide sequence (e.g., at least 5 contiguous Ts, at least 10 contiguous Ts, or at least 15 contiguous Ts).

In some embodiments, the step of generating a cDNA molecule including a sequence that is substantially complementary to the target nucleic acid using a reverse transcription primer can include contacting a permeabilized biological sample with a reverse transcriptase (e.g., any of the exemplary reverse transcriptases described herein or known in the art), dNTPs, and the reverse transcription primer (e.g., any of the exemplary reverse transcription primers described herein). A variety of kits including a reverse transcriptase and dNTPs are commercially available. Non-limiting examples of conditions for generating a cDNA molecule are described herein, and additional examples of conditions for generating a cDNA molecule are known in the art.

In some embodiments of any of the methods described herein, the second adaptor sequence (e.g., ligated to a 3' end of the generated cDNA molecule (performed within the biological sample), or included in the generated cDNA molecule via extension of a 3' end of the cDNA molecule) can have a total of about 5 nucleotides to about 125 nucleotides (or any of the subranges of this range described herein). In some embodiments, the second adaptor sequence can be any predetermined sequence. In some embodiments, the second adaptor sequence does not encode a polypeptide and/or can be non-naturally occurring sequence. In some embodiments, the first and second adaptor sequences include different sequences. In some embodiments, the second adaptor sequence can be a template switching oligonucleotide (TSO) (e.g., any of the exemplary TSOs described herein), or a complement thereof. In some embodiments, the second adaptor sequence includes a sequence that is substantially complementary (e.g., at least 80%, at least 85%, at least 90%, at least 92%, at least 94%, at least 96%, at least 98%, at least 99%, or 100% complementary) to a sequence in the capture domain of the capture probe.

In some embodiments, the step of ligating the second adaptor sequence to a 3' end of the generated cDNA molecule (performed within the biological sample) can be performed using any of the ligation methods described herein or known in the art. A wide variety of different methods can be used for ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end ligations generally do not include hybridization of complementary regions from each nucleic acid molecule because both nucleic acid molecules lack a single-stranded overhang at the site of ligation. In some embodiments, DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, Mass.), and Ampligase® (available from Lucigen, Middleton, Wis.). Derivatives, e.g., sequence-modified derivatives, and/or mutants thereof, can also be used.

For example, the step of ligating can be performed by contacting the permeabilized biological sample with a ligase and the second adaptor sequence (e.g., a TSO), and optionally, any additional components required to accelerate the ligation reaction. In some embodiments, the methods can further include blocking the 5' end of the generated cDNA molecule prior to the ligating step. Non-limiting examples of conditions for performing ligation are described herein, and additional examples of conditions for performing ligation are known in the art.

In some embodiments, extension of a 3' end of a generated cDNA to include a second adaptor sequence can be performed using any appropriate methods, such as those described herein for a TSO. For example, the step of extension of a 3' end of a generated cDNA molecule can include hybridizing an oligo comprising a complement of the second adaptor sequence to a portion of a 3' end of the generated cDNA molecule, and extending the cDNA molecule to include the second adaptor sequence. In some cases, the terminal transferase activity of a reverse transcriptase enzyme will result in a polymononucleotide sequence (e.g., a poly(C) sequence) at the 3' end of a generated cDNA molecule, and the oligo comprising a complement of the second adaptor sequence can further include a complementary polymononucleotide sequence (e.g., a poly(G) sequence) that allows for hybridization to the polymononucleotide sequence of the cDNA molecule. The hybridized oligo comprising the complement of the second adaptor sequence can then be used as a template for extending the 3' end of the generated cDNA molecule to include the second adaptor sequence. In some cases, the oligo comprising a complement of the second adaptor sequence is added to the sample at the same time as the reverse transcription primer.

In some embodiments, the releasing of the cDNA molecule from the target nucleic acid can be performed by using heat or a chemical denaturant (e.g., KOH).

In some embodiments of any of the methods described herein, the array can be any of the types of arrays described herein. For example, the array includes a slide. In some embodiments, the capture probe is attached to the slide (e.g., by its 5' end).

In some embodiments, the array is a bead array. In some embodiments, a 5' end of the capture probe is attached to a bead of the bead array.

In some embodiments, the capture probe further comprises a unique molecular identifier (UMI) (e.g., a UMI positioned 5' relative to the capture domain the capture probe).

In some embodiments, the determining in step (e) comprises sequencing (i) all or a part of the sequence of the target nucleic acid, or a complement thereof, and (ii) all or a part of the sequence of the spatial barcode, or a complement thereof. In some embodiments, the sequencing is high throughput sequencing, sequencing by hybridization, or any of the other methods for sequencing described herein or known in the art. For example, sequencing can involve one or more of nucleic acid amplification, the ligation or addition of one or more sequencing adaptors, cleavage of the capture probe from the array, extension of the capture probe using the bound cDNA as a template, and generating a single-stranded nucleic acid comprising a sequence that is complementary to the extended capture probe. Non-limiting methods for determining the sequence of (i) all or a part of the sequence of the target nucleic acid, or a complement thereof, or (ii) all or a part of the sequence of the spatial barcode, or a complement thereof, are described herein or are known in the art.

In some embodiments, the methods can optionally further include a step of imaging the biological sample (e.g., using any of the exemplary imaging methods described herein or known in the art). In some embodiments, the imaging is performed prior to step (a). In some embodiments, the imaging is performed between steps (b) and (c).

In some embodiments, the method further includes, between steps (b) and (c), a step of freezing and thawing the permeabilized biological sample. In some embodiments, the method can further include, between steps (b) and (c), a step of sectioning (e.g., cryosectioning) the permeabilized biological sample.

EXEMPLARY EMBODIMENTS

FIG. 1A is an exemplary diagram showing, from left to right, the hybridization of a reverse transcription primer to a target nucleic acid, e.g., an mRNA, within a permeabilized biological sample; the generation of a cDNA molecule comprising a sequence that is substantially complementary to the target nucleic acid, and the addition/ligation of a second adaptor sequence (e.g., a template switching oligonucleotide, or a complement thereof) to the 3' end of the cDNA molecule within the permeabilized biological sample; and releasing of the cDNA molecule from the target nucleic acid and contacting the released cDNA molecule to an array (e.g., any of the exemplary arrays described herein) comprising a capture probe for performance of additional steps (e.g., any of the exemplary additional steps described herein). The second adaptor sequence added (e.g., via extension)/ligated to the cDNA specifically binds to the capture probe.

Figure 1B:
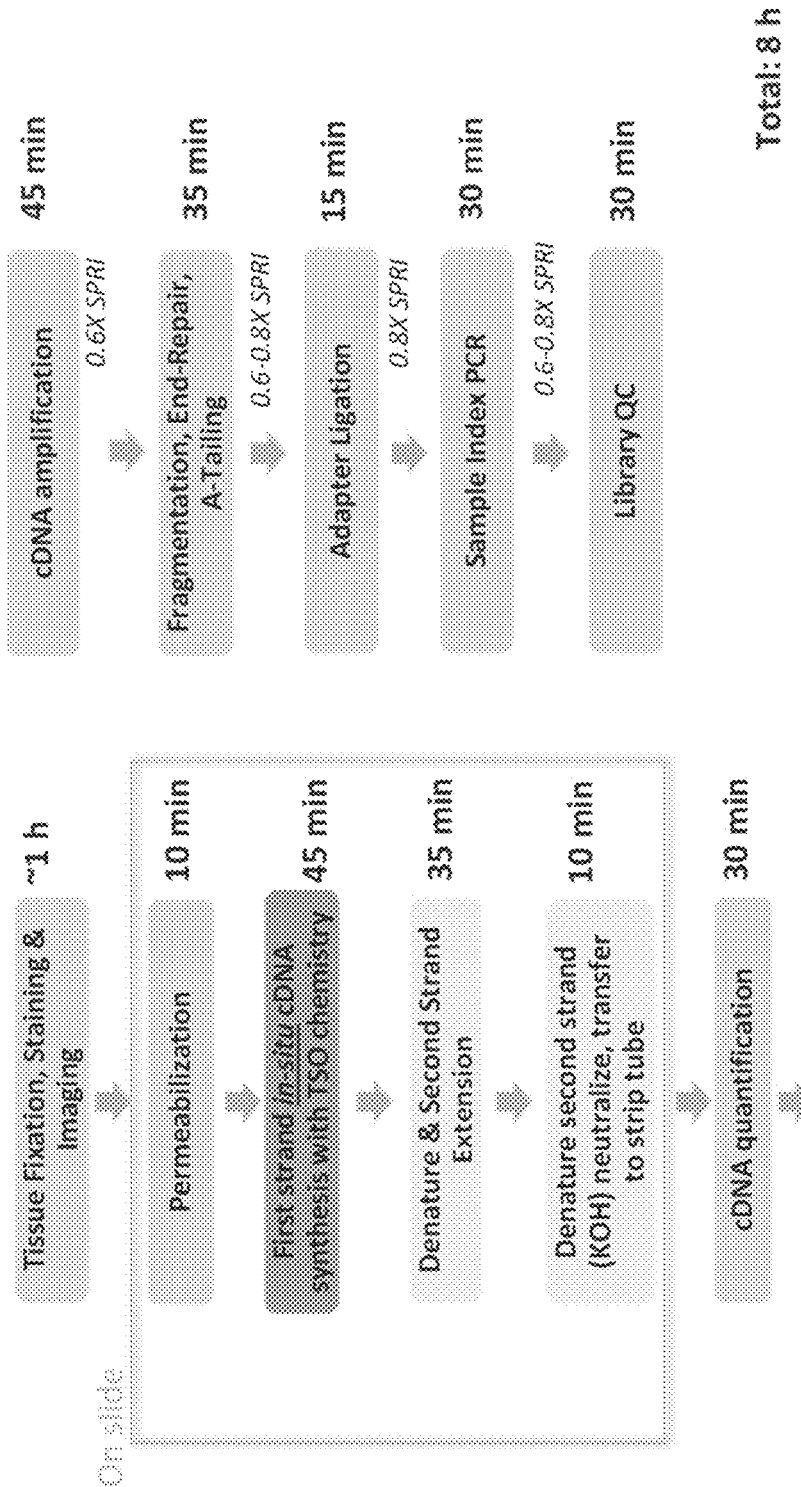
FIG. 1B shows a workflow schematic illustrating exemplary, non-limiting steps for building a 5' spatial gene expression library.

FIG. 1B is an exemplary workflow showing the generation of a gene expression library and the identification of the location of a target nucleic acid in a biological sample, for example following a target analyte capture workflow as shown pictorially in FIG. 1A. Specifically, a biological sample, e.g., a tissue sample, is fixed, stained, and imaged. Any of the exemplary methods described herein or known in the art can be used to fix, stain, and/or image the biological sample. In some embodiments, the biological sample can be a formalin-fixed and paraffin-embedded (FFPE) tissue sample. In some embodiments, the biological sample is stained, e.g., using an H&E staining method. In some embodiments, the tissue sample is fixed, stained, and/or imaged for 5 minutes to about 5 hours, e.g., about 5 minutes to about 4.5 hours, about 5 minutes to about 4.0 hours, about 5 minutes to about 3.5 hours, about 5 minutes to about 3.0 hours, about 5 minutes to about 2.5 hours, about 5 minutes to about 2.0 hours, about 5 minutes to about 1.5 hours, about 5 minutes to about 1.0 hour, about 5 minutes to about 50 minutes, about 5 minutes to about 40 minutes, about 5 minutes to about 30 minutes, about 5 minutes to about 20 minutes, about 5 minutes to about 10 minutes, about 10 minutes to about 5 hours, about 10 minutes to about 4.5 hours, about 10 minutes to about 4.0 hours, about 10 minutes to about 3.5 hours, about 10 minutes to about 3.0 hours, about 10 minutes to about 2.5 hours, about 10 minutes to about 2.0 hours, about 10 minutes to about 1.5 hours, about 10 minutes to about 1.0 hour, about 10 minutes to about 50 minutes, about 10 minutes to about 40 minutes, about 10 minutes to about 30 minutes, about 10 minutes to about 20 minutes, about 20 minutes to about 5 hours, about 20 minutes to about 4.5 hours, about 20 minutes to about 4.0 hours, about 20 minutes to about 3.5 hours, about 20 minutes to about 3.0 hours, about 20 minutes to about 2.5 hours, about 20 minutes to about 2.0 hours, about 20 minutes to about 1.5 hours, about 20 minutes to about 1.0 hour, about 20 minutes to about 50 minutes, about 20 minutes to about 40 minutes, about 20 minutes to about 30 minutes, about 20 minutes to about 5 hours, about 30 minutes to about 4.5 hours, about 30 minutes to about 4.0 hours, about 30 minutes to about 3.5 hours, about 30 minutes to about 3.0 hours, about 30 minutes to about 2.5 hours, about 30 minutes to about 2.0 hours, about 30 minutes to about 1.5 hours, about 30 minutes to about 1.0 hour, about 30 minutes to about 50 minutes, about 30 minutes to about 40 minutes, about 1.0 hour to about 5 hours, about 1.0 hour to about 4.5 hours, about 1.0 hour to about 4.0 hours, about 1.0 hour to about 3.5 hours, about 1.0 hour to about 3.0 hours, about 1.0 hour to about 2.5 hours, about 1.0 hour to about 2.0 hours, about 1.0 hour to about 1.5 hours, about 1.5 hour to about 5 hours, about 1.5 hour to about 4.5 hours, about 1.5 hour to about 4.0 hours, about 1.5 hour to about 3.5 hours, about 1.5 hour to about 3.0 hours, about 1.5 hour to about 2.5 hours, about 1.5 hour to about 2.0 hours, about 2.0 hour to about 5 hours, about 2.0 hour to about 4.5 hours, about 2.0 hour to about 4.0 hours, about 2.0 hour to about 3.5 hours, about 2.0 hour to about 3.0 hours, about 2.0 hour to about 2.5 hours, about 2.5 hour to about 5 hours, about 2.5 hour to about 4.5 hours, about 2.5 hour to about 4.0 hours, about 2.5 hour to about 3.5 hours, about 2.5 hour to about 3.0 hours, about 3.0 hour to about 5 hours, about 3.0 hour to about 4.5 hours, about 3.0 hour to about 4.0 hours, about 3.0 hour to about 3.5 hours, about 3.5 hour to about 5 hours, about 3.5 hour to about 4.5 hours, about 3.5 hour to about 4.0 hours, about 4.0 hour to about 5 hours, about 4.0 hour to about 4.5 hours, or about 4.5 hour to about 5 hours.

After the fixation, staining and imaging of the biological sample, the biological sample is permeabilized. Permeabilization of the biological sample (e.g., a tissue sample) can be performed using any of the exemplary methods or exemplary reagents described herein, or in, e.g., Section (I)(d)(ii)(13) of WO 2020/176788 and/or U.S. Patent Application Publication No. 2020/0277663. In some embodiments, the permeabilization of the biological sample (e.g., tissue sample) can be performed for about 1 minute to about 5 hours (e.g., about 1 minute to about 4.5 hours, about 1 minute to about 4.0 hours, about 1 minute to about 3.5 hours, about 1 minute to about 3.0 hours, about 1 minute to about 2.5 hours, about 1 minute to about 2.0 hours, about 1 minute to about 1.5 hours, about 1 minute to about 1.0 hour, about 1 minute to about 50 minutes, about 1 minute to about 40 minutes, about 1 minute to about 30 minutes, about 1 minute to about 20 minutes, about 1 minute to about 10 minutes, about 1 minute to about 5 minutes, about 10 minutes to about 5.0 hours, about 10 minutes to about 4.5 hours, about 10 minutes to about 4.0 hours, about 10 minutes to about 3.5 hours, about 10 minutes to about 3.0 hours, about 10 minutes to about 2.5 hours, about 10 minutes to about 2.0 hours, about 10 minutes to about 1.5 hours, about 10 minutes to about 1.0 hour, about 10 minutes to about 50 minutes, about 10 minutes to about 40 minutes, about 10 minutes to about 30 minutes, about 10 minutes to about 20 minutes, about 20 minutes to about 5.0 hours, about 20 minutes to about 4.5 hours, about 20 minutes to about 4.0 hours, about 20 minutes to about 3.5 hours, about 20 minutes to about 3.0 hours, about 20 minutes to about 2.5 hours, about 20 minutes to about 2.0 hours, about 20 minutes to about 1.5 hours, about 20 minutes to about 1.0 hour, about 20 minutes to about 50 minutes, about 20 minutes to about 40 minutes, about 20 minutes to about 30 minutes, about 30 minutes to about 5.0 hours, about 30 minutes to about 4.5 hours, about 30 minutes to about 4.0 hours, about 30 minutes to about 3.5 hours, about 30 minutes to about 3.0 hours, about 30 minutes to about 2.5 hours, about 30 minutes to about 2.0 hours, about 30 minutes to about 1.5 hours, about 30 minutes to about 1.0 hour, about 30 minutes to about 50 minutes, about 30 minutes to about 40 minutes, about 1.0 hour to about 5.0 hours, about 1.0 hour to about 4.5 hours, about 1.0 hour to about 4.0 hours, about 1.0 hour to about 3.5 hours, about 1.0 hour to about 3.0 hours, about 1.0 hour to about 2.5 hours, about 1.0 hour to about 2.0 hours, about 1.0 hour to about 1.5 hours, about 2.0 hours to about 5.0 hours, about 2.0 hours to about 4.5 hours, about 2.0 hours to about 4.0 hours, about 2.0 hours to about 3.5 hours, about 2.0 hours to about 3.0 hours, about 2.0 hours to about 2.5 hours, about 3.0 hours to about 5.0 hours, about 3.0 hours to about 4.5 hours, about 3.0 hours to about 4.0 hours, about 3.0 hours to about 3.5 hours, about 4.0 hours to about 5.0 hours, about 4.0 hours to about 4.5 hours, or about 4.5 hours to about 5.0 hours).

After permeabilization of the biological sample, the target nucleic acid in the permeabilized biological sample is contacted and hybridized with a reverse transcription primer (e.g., any of the reverse transcription primers described herein) to generate a cDNA molecule comprising a sequence that is substantially complementary to the target nucleic acid.

In some embodiments, after the generation of the cDNA molecule, a second adaptor sequence is ligated to the 3' end of the cDNA molecule. Any suitable adaptor sequence described herein can be ligated to the 3' end of the cDNA molecule. In some embodiments, the second adaptor molecule is a template switching oligonucleotide (TSO).

In some embodiments, a 3' end of the cDNA molecule is extended to include a second adaptor sequence. Any adaptor sequence described herein can be included to the 3' end of the cDNA molecule. In some embodiments, the second adaptor molecule is a template switching oligonucleotide (TSO), or a complement thereof.

The generation of the cDNA molecule and the addition (e.g., via extension) or ligation of the second adaptor sequence can be performed over about 1 minute to about 2 hours (e.g., about 1 minute to about 1.5 hours, about 1 minute to about 1.0 hour, about 1 minute to about 40 minutes, about 1 minute to about 20 minutes, about 1 minute to about 10 minutes, about 10 minutes to about 2.0 hours, about 10 minutes to about 1.5 hours, about 10 minutes to about 1.0 hour, about 10 minutes to about 40 minutes, about 10 minutes to about 20 minutes, about 20 minutes to about 2.0 hours, about 20 minutes to about 1.5 hours, about 20 minutes to about 1.0 hour, about 20 minutes to about 40 minutes, about 40 minutes to about 2.0 hours, about 40 minutes to about 1.5 hours, about 40 minutes to about 1.0 hour, about 1.0 hour to about 2.0 hours, about 1 hour to about 1.5 hours, or about 1.5 hours to about 2.0 hours).

In some embodiments, the reverse transcription occurs within the permeabilized biological sample, e.g., a permeabilized tissue sample. In some embodiments, the permeabilization and the generation of the cDNA molecule occurs while the biological sample is disposed on the array.

After the generation of the cDNA molecule and the addition (e.g., via extension) or ligation of the second adaptor sequence, the cDNA molecule can be denatured/released from the target nucleic acid and the cDNA molecule is contacted with an array comprising a capture probe. The capture probe can include in a 5' to a 3' direction: (i) a spatial barcode and (ii) a capture domain that binds specifically to the second adaptor sequence ligated to the cDNA. When contacting with the array with the cDNA molecule, the attached capture probe captures the cDNA molecule using the capture domain, and the 3' end of the capture probe is extended to add a sequence that is substantially complementary to the cDNA molecule sequence. In some embodiments, the methods can further include generating a single-stranded nucleic acid that includes a sequence that is substantially complementary to the extended capture probe. The optional steps of extending a 3' end of the capture probe (using the specifically bound cDNA as a template) and generating a single-stranded nucleic acid including a sequence complementary to the extended capture probe can be performed for about 5 minutes to about 2 hours (or any of the subranges within this range described herein).

In some embodiments, a single-stranded nucleic acid including a sequence complementary to the extended capture probe can be denatured from the extended capture probe, and optionally, transferred to a different tube or container for performance of additional steps.

The single-stranded nucleic acid including a sequence complementary to the extended capture probe can be quantitated and/or sequenced or at least partially sequenced using any of the methods described herein, or described in, e.g., Sections (II)(a) or (II)(g) (e.g., (II)(g)(iv)) of WO 2020/176788 and/or U.S. Patent Application Publication No. 2020/0277663 or known in the art. In some embodiments, the quantitation and/or sequencing of the single-stranded nucleic acid including a sequence complementary to the extended capture probe can be quantitated and/or sequenced or at least partially sequenced for about 10 minutes to about 2 hours (or any of the subranges of this range described herein).

Following the denaturing of the single-stranded nucleic acid including a sequence complementary to the extended capture probe, the single-stranded nucleic acid including the sequence complementary to the extended capture probe can be subjected to amplification, fragmentation, end-repairing, A-tailing, adaptor ligation, sample index PCR, and the construction and quality control of a gene expression library, using any of the exemplary methods described herein, or described in, e.g., Sections (II)(a) or (II)(g) (e.g., (II)(g)(iv)) of WO 2020/176788 and/or U.S. Patent Application Publication No. 2020/0277663.

Figure 2A:
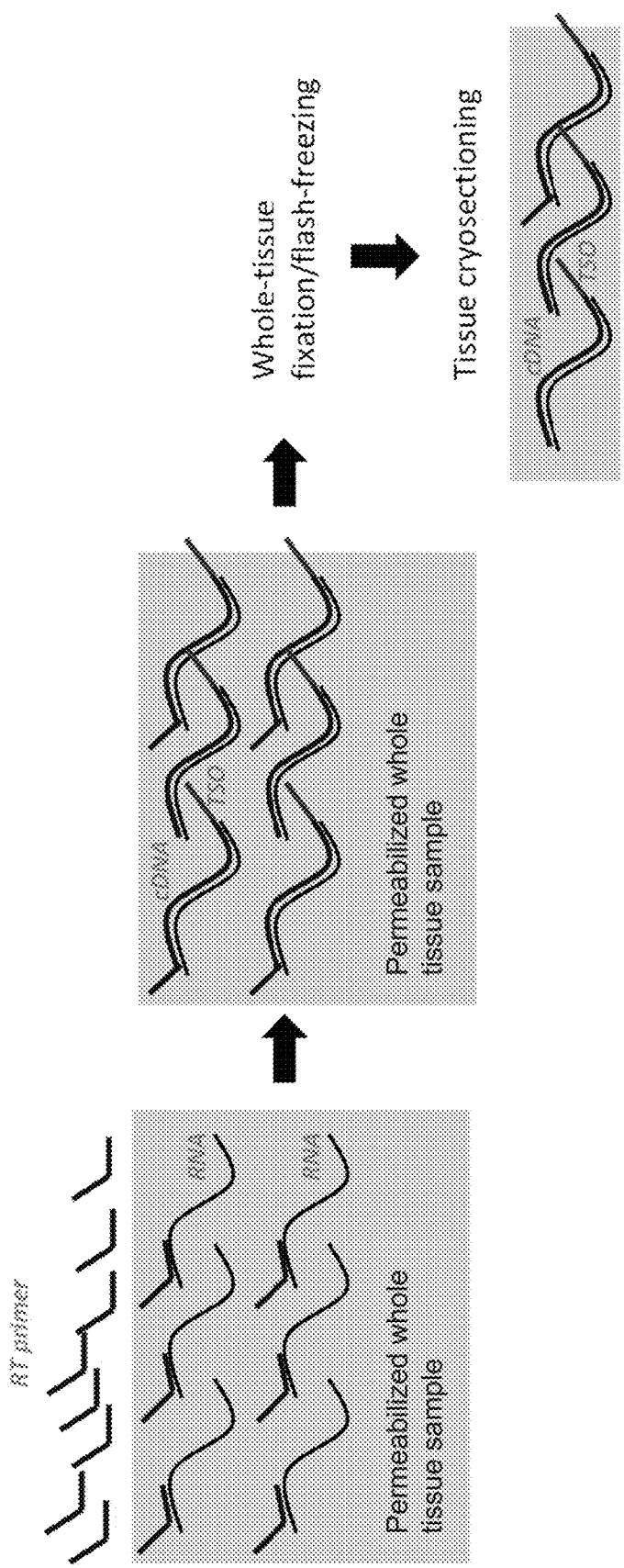
FIG. 2A shows a workflow schematic illustrating exemplary, non-limiting steps for in-situ cDNA synthesis and sample handling.

FIG. 2A is an exemplary diagram showing, from left to right, the hybridization of a reverse transcription primer to a target nucleic acid, e.g., an mRNA, within a permeabilized biological sample, e.g., a whole tissue sample that has not been sectioned, cut or further fragmented; the generation of a cDNA molecule comprising a sequence that is substantially complementary to the target nucleic acid, and the addition (e.g., via extension) or ligation of a second adaptor sequence (e.g., a template switching oligonucleotide, or a complement thereof) to the 3' end of the cDNA molecule within the permeabilized biological sample, e.g., a whole tissue sample that has not been sectioned, cut or further fragmented; the fixation and/or flash-freezing of the biological sample, and the cryosectioning of the whole tissue sample for use in additional steps. When using a whole tissue sample that has not been sectioned, cut or further fragmented, the steps described in FIG. 2A are performed when the biological sample is not disposed on an array.

Figure 2B:
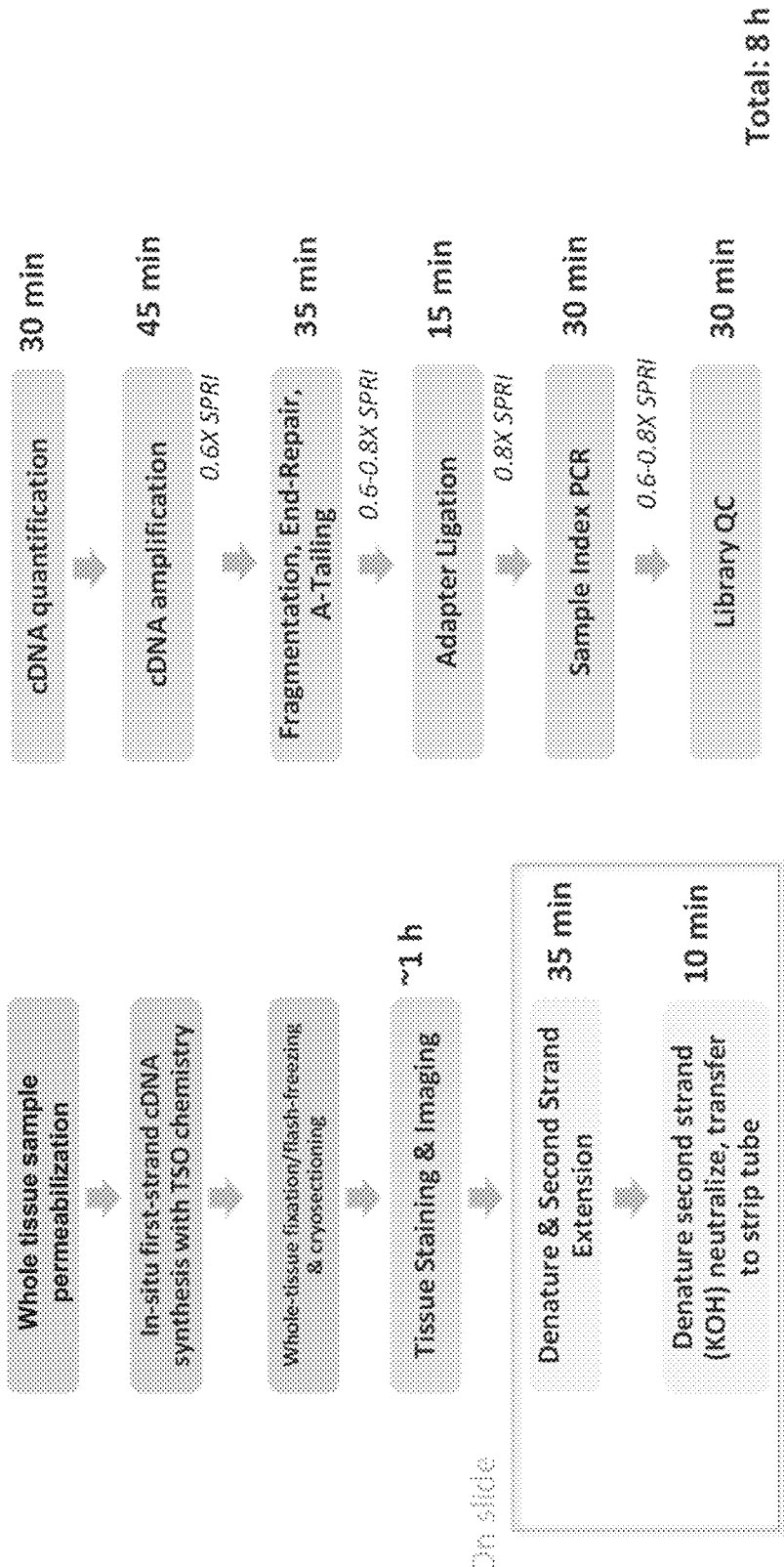
FIG. 2B shows a workflow schematic illustrating exemplary, non-limiting steps for building a 5' spatial gene expression library.

FIG. 2B is an exemplary workflow showing the generation of a gene expression library and the identification of the location of a target nucleic acid in a biological sample, for example following the target analyte capture workflow of FIG. 2A. Specifically, a biological sample, e.g., a whole tissue sample, is permeabilized. Any suitable permeabilization method described herein, or in, e.g., Section (I)(d)(ii)(13) of WO 2020/176788 and/or U.S. Patent Application Publication No. 2020/0277663, or known in the art can be used to permeabilize the whole tissue sample. In some embodiments, the biological sample is permeabilized for about 5 minutes to about 5 hours (or any of the subranges of this range described herein).

After permeabilization of the biological sample, the target nucleic acid in the permeabilized biological sample is contacted and annealed with a reverse transcription primer to generate a cDNA molecule comprising a sequence that is substantially complementary to the target nucleic acid. After synthesis of the cDNA molecule, a second adaptor sequence is added (e.g., via extension) or ligated to the 3' end of the cDNA molecule. Any suitable adaptor sequence described in the current application can be used to ligate to the 3' cDNA molecule. In some embodiments, the second adaptor molecule is a template switching oligonucleotide (TSO), or a complement thereof. The generation of the cDNA molecule and the addition (e.g., via extension) or ligation of the second adaptor sequence can be performed for about 10 minutes to about 2 hours (or any of the subranges of this range described herein). In some embodiments, the synthesis of the cDNA molecule occurs within a permeabilized whole tissue sample.

Following the generation of the cDNA molecule, the biological sample, e.g., the whole tissue sample, can be fixed and/or flash-frozen. Any suitable methods described herein, or in, e.g., Section (I)(d)(1)-(I)(d)(4) of WO 2020/176788 and/or U.S. Patent Application Publication No. 2020/0277663, or known in the art can be used to fix and flash-freeze the tissue sample. In some embodiments, the biological sample, e.g., the whole tissue sample is formalin-fixed and paraffin-embedded (FFPE). In some embodiments, the biological sample, e.g., whole tissue sample, is flash-frozen using liquid nitrogen. The flash-frozen tissue sample is then sectioned for future steps. In some embodiments, the sectioning is performed using cryosectioning. In some embodiments, the methods further comprise a thawing step, after the cryosectioning.

After sectioning, the biological sample, e.g., tissue sample, can be stained, and imaged. Any of the methods described herein, or in, e.g., Section (I)(d)(6) or (II)(a)(i) of WO 2020/176788 and/or U.S. Patent Application Publication No. 2020/0277663, or known in the art can be used to stain and/or image the biological sample. In some embodiments, the biological sample is stained using an H&E staining method. In some embodiments, the tissue sample is stained and imaged for about 10 minutes to about 2 hours (or any of the subranges of this range described herein). Additional time may be needed for staining and imaging of different types of biological samples.

In some embodiments, the generation of the cDNA occurs within the permeabilized biological sample, e.g., a permeabilized tissue sample. In some embodiments, the permeabilization and the generation of the cDNA occurs while the biological sample is not disposed on the array.

After the generation of the cDNA molecule, the addition (e.g., via extension) or ligation of the second adaptor sequence to a 3' end of the cDNA, and the tissue fixation, freezing, sectioning, staining, and imaging, the cDNA is released/denatured from the target nucleic acid and the cDNA is contacted with an array comprising a capture probe. The capture probe can include in a 5' to a 3' direction: (i) a spatial barcode and (ii) a capture domain that binds specifically to the second adaptor sequence ligated to the cDNA. When the array is contacted with the cDNA, the capture probe binds specifically to the cDNA via the capture domain, and the 3' end of the capture probe is extended (using the specifically bound cDNA as a template) to add a sequence that is substantially complementary to the cDNA. The method can further include generating a single-stranded nucleic acid that is complementary to the extended capture probe. The denaturing of the cDNA from the target nucleic acid, the extension of the capture probe (using the specifically bound cDNA as a template), and optional generation of a single-stranded nucleic acid including a sequence that is complementary to the extended capture probe can be performed over 10 minutes to about 5 hours (or any of the subranges of this range described herein).

The single-stranded nucleic acid including a sequence that is complementary to the extended capture probe can be separated/denatured from the extended capture probe and optionally, transferred to a container (e.g., a strip tube) for the performance of additional steps.

The extended capture probe and/or a denatured/separated single-stranded nucleic acid including a sequence that is complementary to the extended capture probe can be quantitated and/or sequenced or at least partially sequenced using any of the methods described herein, or described in, e.g., Sections (II)(a) or (II)(g) (e.g., (II)(g)(iv)) of WO 2020/176788 and/or U.S. Patent Application Publication No. 2020/0277663 or known in the art. In some embodiments, the quantitation and/or sequencing of the extended capture probe and/or a denatured/separated single-stranded nucleic acid including a sequence that is complementary to the extended capture probe can be performed for about 10 minutes to about 5 hours (or any of the subranges of this range described herein).

Following the denaturing of the single-stranded nucleic acid including a sequence complementary to the extended capture probe, the single-stranded nucleic acid including the sequence complementary to the extended capture probe can be subjected to amplification, fragmentation, end-repairing, A-tailing, adaptor ligation, sample index PCR, and the construction and quality control of a gene expression library, using any of the exemplary methods described herein, or described in, e.g., Sections (II)(a) or (II)(g) (e.g., (II)(g)(iv)) of WO 2020/176788 and/or U.S. Patent Application Publication No. 2020/0277663.

Figure 3A:
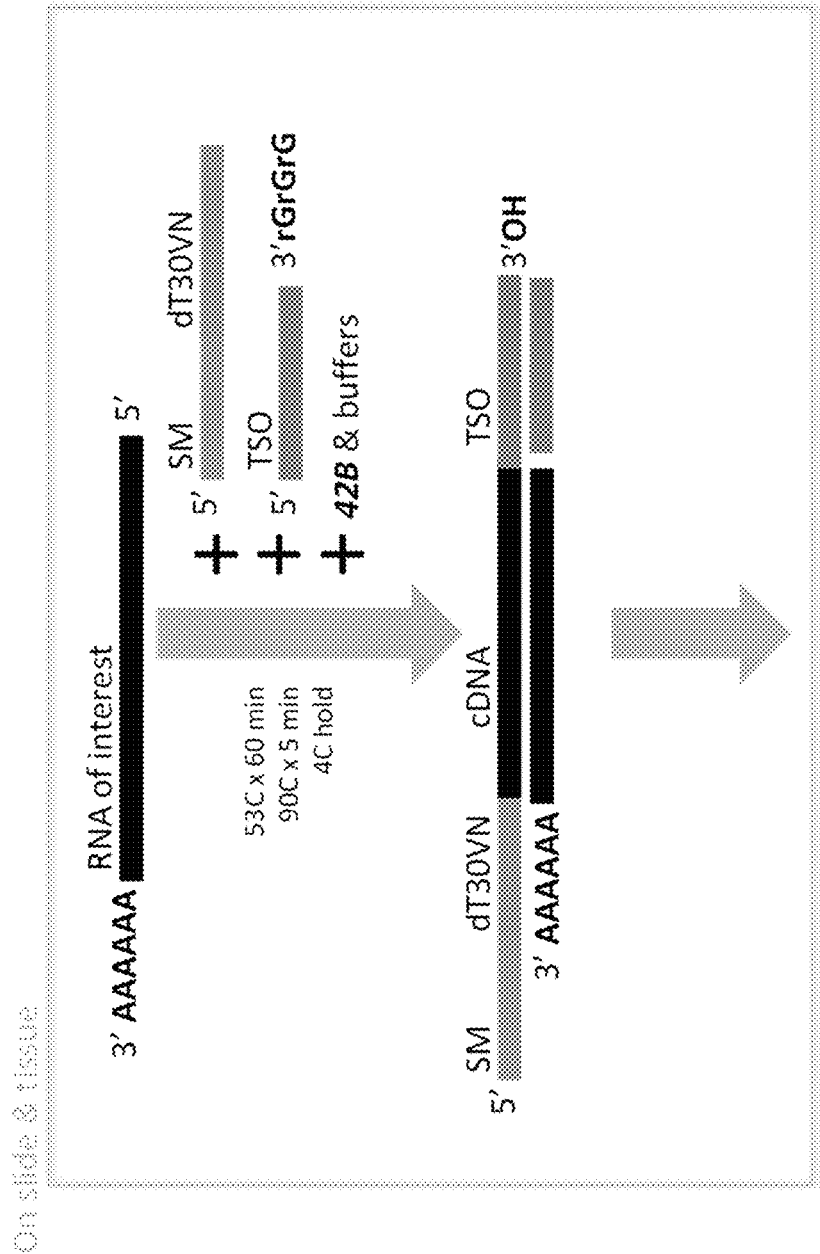
FIG. 3A shows a workflow schematic illustrating exemplary, non-limiting steps for synthesizing a cDNA molecule.

FIG. 3A is a diagram showing an exemplary reaction mix that can be used to generate a cDNA and that can be used to add (e.g., via extension) or ligate a second adaptor sequence to a 3' end of the cDNA. For example, a target nucleic acid in the biological sample can be an mRNA molecule having a poly(A) tail at the 3' end of the sequence. For the generation of a cDNA, a reverse transcription primer is added to the biological sample. The reverse transcription primer includes, from the 5' end to the 3' end, a first adaptor sequence (SM), and a sequence that is substantially complementary to a portion of the mRNA. In some embodiments, the sequence that is substantially complementary to a portion of the mRNA includes a poly(T) sequence comprising a sequence of $T_n$, wherein n can be 3, 4, 5, 6, 7, 8, 9, 10, 11, 12, 13, 14, 15, 16, 17, 18, 19, 20, 21, 22, 23, 24, 25, 26, 27, 28, 29, or 30. In some embodiments, the sequence substantially complementary to a portion of the mRNA is a dT30VN sequence, where the sequence comprises $T_n$, wherein n is 30, wherein V is A, G, or C, and where N is A, G, C, or T. In some embodiments, the sequence substantially complementary to a portion of the mRNA can includes a random sequence.

In some embodiments, the complement of the second adaptor sequence can be added to a reverse transcription mix. In some embodiments, the complement of the second adaptor sequence can be a template switching oligonucleotide (TSO) having a rGrGrG sequence at the 3' end of the second adaptor sequence.

The reverse transcription step can be performed using a method that includes a pre-equilibration thermocycling protocol (e.g., lid temperature and pre-equilibration at about 53° C., reverse transcription at about 53° C. for about 60 minutes, about 90° C. for about 5 min, and then held at about 4° C.). Any suitable reverse transcriptase and buffers can be used to perform reverse transcription, such as any of those described herein or known in the art. In some embodiments, the reverse transcription mix can further include other components that assist or increase the rate of a reverse transcription reaction. For example, the reverse transcription mix can further include dNTPs. The thermocycling protocol for the reverse transcription reaction and the ligation of the second adaptor sequence to the 3' end of the cDNA can be further optimized according to different target nucleic acids in different types of biological samples.

The reaction described in FIG. 3A generates a cDNA comprising, for the 5' end to the 3' end, a first adaptor sequence (e.g., SM sequence), a sequence substantially complementary to the target nucleic acid (e.g., a dT30VN sequence), a sequence complementary to the target nucleic acid sequence, and a complement of a second adaptor sequence (e.g., a TSO sequence). In some embodiments, the cDNA is hybridized to the target nucleic acid molecule is subsequently denatured/separated from the nucleic acid analyte.

Figure 3B:
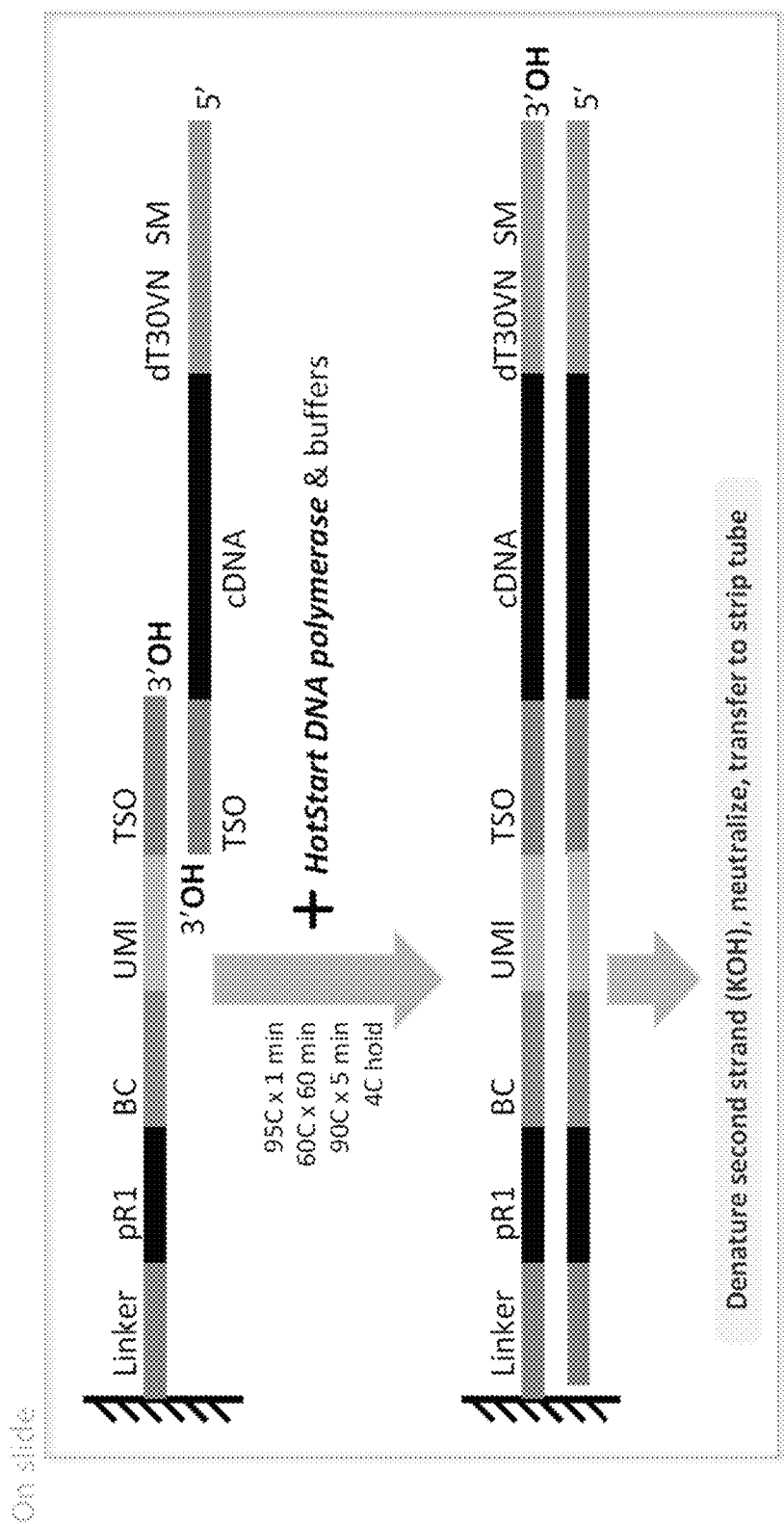
FIG. 3B shows a workflow schematic illustrating exemplary, non-limiting steps for cDNA binding to an attached capture probe and the extension of the capture probe using the cDNA molecule as a template, and the generation of a second strand complementary to the extended capture probe.

FIG. 3B is a diagram showing an exemplary array comprising a second exemplary capture probe. The capture probe comprises, from the 5' end to the 3' end, a linker sequence, a partial R1 primer sequence, a spatial barcode, a unique molecular identifier (UMI), a capture domain, e.g., a sequence substantially complementary to the second adaptor sequence. In some embodiments the sequence substantially complementary to the second adaptor sequence is substantially complementary to a template switching oligonucleotide (TSO) ligated to the cDNA molecule. In some embodiments the sequence substantially complementary to the second adaptor sequence is comprises a template switching oligonucleotide (TSO) used as a template for extension of a 3' end of the cDNA molecule. In some embodiments, the 5' end of the capture probe is attached to the array. After the capture domain on the capture probe specifically binds to the second adaptor sequence on the cDNA molecule, a 3' end of the capture probe is extended (using the specifically bound cDNA as a template) to add a sequence that is substantially complementary to the sequence of the cDNA and a sequence complementary to the first adaptor sequence). In addition, a single-stranded nucleic acid that includes a sequence that is complementary to the extended capture probe can be generated (bottom strand shown in bottom half of figure).

The generation of the extended capture probe and the generation of the single-stranded nucleic acid that includes a sequence complementary to the extended capture probe in FIG. 3B can be performed using a thermocycling protocol (e.g., lid temperature and pre-equilibrate at about 95° C., denaturing at about 95° C. for about 1 min, reannealing at about 60° C. for about 60 min, extension at about 90° C. for about 5 minutes, and then held at about 4° C.). The reaction mixture further includes all necessary polymerase and buffers. In some embodiments, the polymerase can be a DNA polymerase. In some embodiments, the DNA polymerase can be HotStart Taq DNA polymerase.

After the generation of the single-stranded nucleic acid including a sequence that is complementary to the extended capture probe, KOH can be added to denature the single-stranded nucleic acid including a sequence complementary to the extended capture probe from the extended capture probe, and transferring the single-stranded nucleic acid including a sequence that is complementary to the extended capture probe to a different tube (e.g., one or more tubes, for example a strip tube that might be used in a thermocyling instrument) for the performance of additional steps.

Figure 3C:
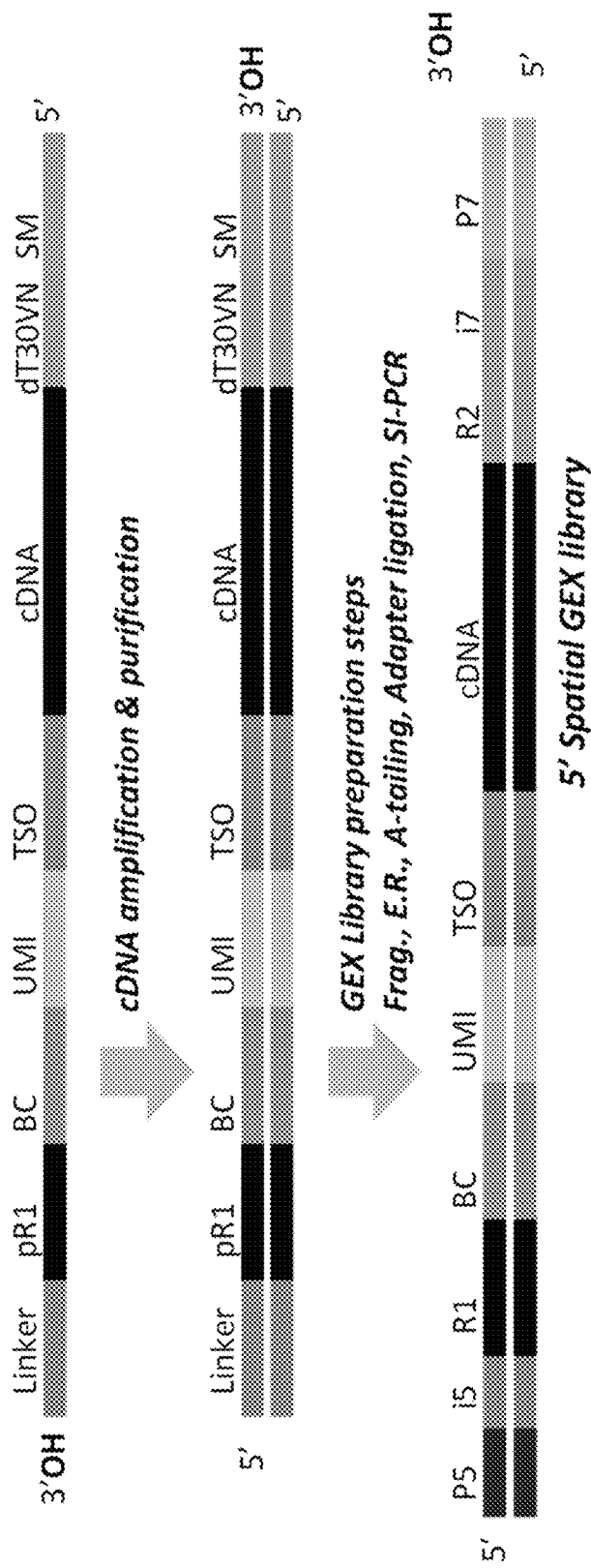
FIG. 3C shows a workflow schematic illustrating exemplary, non-limiting, non-exhaustive steps for building a 5' spatial gene expression library.

FIG. 3C is a diagram showing exemplary steps of amplification, quantitation, and/or sequencing of a single-stranded nucleic acid that includes a sequence complementary to the extended capture probe. In some embodiments, the methods can include the performance of qPCR. Exemplary methods for performing qPCR are described herein and are known in the art.

In some embodiments, the method can result in the generation of a single-stranded nucleic acid that includes in a 5' to a 3' direction, a linker, a partial R1 primer sequence, a spatial barcode, a UMI, a sequence complementary to the second adaptor sequence, a sequence present in the target nucleic acid, and a sequence complementary to the first adaptor sequence.

In some embodiments, the method can result in the generation of a single-stranded nucleic acid that includes in a 5' to a 3' direction, a P5 sequencing handle, a i5 sequencing handle, a linker, a partial R1 or R1 primer sequence, a spatial barcode, a UMI, a sequence complementary to the second adaptor sequence, a sequence present in the target nucleic acid, a R2 adaptor sequence, an i7 sequencing handle, and a P7 sequencing handle.

In some embodiments, the method can result in the generation of a single-stranded nucleic acid that includes in a 3' to a 5' direction, a sequence complementary to a linker, a sequence complementary to a partial R1 primer sequence, a sequence complementary to a spatial barcode, a sequence complementary to a UMI, the second adaptor sequence, a sequence complementary to a sequence present in the target nucleic acid, and the first adaptor sequence.

In some embodiments, the method can result in the generation of a single-stranded nucleic acid that includes in a 3' to a 5' direction, a sequence complementary to a P5 sequencing handle, a sequence complementary to an i5 sequencing handle, a sequence complementary to a linker, a sequence complementary to a partial R1 or R1 primer sequence, a sequence complementary to a spatial barcode, a sequence complementary to a UMI, the second adaptor sequence, a sequence complementary to a sequence present in the target nucleic acid, a sequence complementary to an R2 adaptor sequence, a sequence complementary to an i7 sequencing handle, and a sequence complementary to a P7 sequencing handle.

In some embodiments of any of the methods described herein, step (e) includes sequencing all or a part of the sequence of the spatial barcode, or a complement thereof, and sequencing all of a part of the sequence of the target nucleic acid, or a complement thereof. The sequencing can be performed using any of the methods described herein. In some embodiments, step (e) includes sequencing the full-length sequence of the spatial barcode, or a complement thereof. In some embodiments, step (e) includes sequencing a part of the sequence of the spatial barcode, or a complement thereof. In some embodiments, step (e) includes sequencing the full-length sequence of the target nucleic acid, or a complement thereof. In some embodiments, step (e) includes sequencing a part of the target nucleic acid, or a complement thereof. In some embodiments, the sequencing is performed using high throughput sequencing. In some embodiments, the target nucleic acid is sequenced from the 5' end of the target nucleic acid. In some embodiments, the target nucleic acid is sequenced from the 3' end of the target nucleic acid. In some embodiments, the target nucleic acid is sequenced from both the 3' end and the 5' end of the target nucleic acid. The library can be sequenced using available sequencing platforms, including, any of MiSeq, NextSeq 500/550, HiSeq 2500, HiSeq 3000/4000, NovaSeq, or iSeq.

Kits

Also provided herein are kits for performing any of the methods described herein. For example, provided herein is a kit comprising: a reverse transcription primer comprising (i) a sequence that is substantially complementary to a portion of the target nucleic acid and (ii) a first adaptor sequence; a reverse transcriptase; and an oligonucleotide comprising a second adaptor sequence or a complement thereof. In some embodiments, the reverse transcriptase is a reverse transcriptase with terminal transferase activity. In some embodiments, the second adaptor sequence or complement thereof is a TSO or complement thereof. The kits can include any other buffers, enzymes, cofactors, or other components useful in the method. For example, when the method includes ligating the second adaptor sequence to the generated cDNA molecule, the kit can further include a ligase. In some embodiments, the kits can also include an array, wherein the array comprises an attached capture probe comprising in a 5' to a 3' direction: (i) a spatial barcode and (ii) a capture domain that binds specifically to the second adaptor sequence. In some examples, the kit can further include a permeabilizing agent. In some embodiments, the kit can further include a lipase, a protease, and/or an RNAse.

EXEMPLARY EMBODIMENTS

Embodiment 1 is a method of identifying a location of a target nucleic acid in a permeabilized biological sample, the method comprising:
  (a) generating a cDNA molecule comprising a sequence that is substantially complementary to the target nucleic acid using a reverse transcription primer comprising (i) a sequence that is substantially complementary to a portion of the target nucleic acid and (ii) a first adaptor sequence, wherein the step of generating the cDNA molecule occurs within the permeabilized biological sample;
  (b) ligating a second adaptor sequence to a 3' end of the cDNA molecule, wherein the step of ligating is performed within the biological sample;
  (c) releasing the cDNA molecule from the target nucleic acid, such that the cDNA contacts an array, wherein the array comprises an attached capture probe comprising in a 5' to a 3' direction: (i) a spatial barcode and (ii) a capture domain that binds specifically to the second adaptor sequence ligated to the cDNA;
  (d) extending a 3' end of the capture probe using the cDNA as a template; and
  (e) determining (i) all or a part of the sequence of the target nucleic acid, or a complement thereof, and (ii) all or a part of the sequence of the spatial barcode, or a complement thereof, and using the determined sequences of (i) and (ii) to identify the location of the target nucleic acid in the permeabilized biological sample.

Embodiment 2 is a method of identifying a location of a target nucleic acid in a permeabilized biological sample, the method comprising:

(a) generating a cDNA molecule comprising a sequence that is substantially complementary to the target nucleic acid using a reverse transcription primer comprising (i) a sequence that is substantially complementary to a portion of the target nucleic acid and (ii) a first adaptor sequence, wherein the step of generating the cDNA molecule occurs within the permeabilized biological sample;
(b) extending a 3' end of the cDNA molecule to include a second adaptor sequence, wherein the step of extending is performed within the biological sample;
(c) releasing the cDNA molecule from the target nucleic acid, such that the cDNA contacts an array, wherein the array comprises an attached capture probe comprising in a 5' to a 3' direction: (i) a spatial barcode and (ii) a capture domain that binds specifically to the second adaptor sequence;
(d) extending a 3' end of the capture probe using the cDNA as a template; and
(e) determining (i) all or a part of the sequence of the target nucleic acid, or a complement thereof, and (ii) the sequence of the spatial barcode, or a complement thereof, and using the determined sequences of (i) and (ii) to identify the location of the target nucleic acid in the permeabilized biological sample.

Embodiment 3 is the method of Embodiment 2, wherein step (b) occurs simultaneously with step (a).

Embodiment 4 is the method of any one of Embodiments 1-3, wherein steps (a) through (c) are performed when the biological sample is disposed on the array.

Embodiment 5 is the method of any one of Embodiments 1-3, wherein step (a) is performed when the biological sample is not disposed on the array and step (b) is performed when the biological sample is disposed on the array, and wherein the method further comprises between steps (a) and (b), a step of disposing the biological sample on the array.

Embodiment 6 is the method of any one of Embodiments 1-3, wherein steps (a) and (b) are performed when the biological sample is not disposed on the array, and wherein the method further comprises between steps (b) and (c), a step of disposing the biological sample on the array.

Embodiment 7 is the method of any one of Embodiments 1-6, wherein the sequence that is substantially complementary to a portion of the target nucleic acid present in the reverse transcription primer comprises a poly(T) sequence.

Embodiment 8 is the method of any one of Embodiments 1-6, wherein the sequence that is substantially complementary to a portion of the target nucleic acid present in the reverse transcription primer comprises a random sequence.

Embodiment 9 is the method of any one of Embodiments 1-8, wherein the second adaptor sequence is a template switching oligonucleotide (TSO), or a complement thereof.

Embodiment 10 is the method of any one of Embodiments 1-9, wherein the array comprises a slide.

Embodiment 11 is the method of Embodiment 10, wherein a 5' end of the capture probe is attached to the slide.

Embodiment 12 is the method of any one of Embodiments 1-9, wherein the array is a bead array.

Embodiment 13 is the method of Embodiment 12, wherein a 5' end of the capture probe is attached to a bead of the bead array.

Embodiment 14 is the method of any one of Embodiments 1-13, wherein the capture probe further comprises a unique molecular identifier (UMI).

Embodiment 15 is the method of Embodiment 14, wherein the UMI is positioned 5' relative to the capture domain in the capture probe.

Embodiment 16 is the method of any one of Embodiments 1-15, wherein the determining in step (e) comprises sequencing (i) all or a part of the sequence of the target nucleic acid, or a complement thereof, and (ii) the sequence of the spatial barcode, or a complement thereof.

Embodiment 17 is the method of Embodiment 16, wherein the sequencing is high throughput sequencing.

Embodiment 18 is the method of Embodiment 16, wherein the sequencing is sequencing by hybridization.

Embodiment 19 is the method of any one of Embodiments 1-18, wherein the target nucleic acid is RNA.

Embodiment 20 is the method of Embodiment 19, wherein the RNA is an mRNA.

Embodiment 21 is the method of any one of Embodiments 1-20, wherein the permeabilized biological sample is a permeabilized tissue section.

Embodiment 22 is the method of Embodiment 21, wherein the permeabilized tissue section is a permeabilized formalin-fixed and paraffin-embedded (FFPE) tissue section.

Embodiment 23 is the method of any one of Embodiments 1-22, wherein the method further comprises a step of imaging the biological sample.

Embodiment 24 is the method of Embodiment 23, wherein the step of imaging is performed prior to step (a).

Embodiment 25 is the method of Embodiment 24, wherein the step of imaging is performed between steps (b) and (c).

Embodiment 26 is the method of any one of Embodiments 1-3 and 6-25, wherein the method further comprises, between steps (b) and (c), a step of freezing and thawing the permeabilized biological sample.

Embodiment 27 is the method of Embodiment 26, wherein the method further comprises, between steps (b) and (c), a step of sectioning the permeabilized biological sample.

Embodiment 28 is the method of Embodiment 27, wherein the step of sectioning the permeabilized biological sample is performed using cryosectioning.

Embodiment 29 is the method of any one of Embodiments 1-28, wherein the method further comprises, prior to step (a), a step of permeabilizing the biological sample.

Embodiment 30 is the method of any one of Embodiments 1-29, wherein the performance of step (a) comprises introducing a reverse transcriptase, dNTPs, and the reverse transcription primer into the permeabilized biological sample.

Embodiment 31 is a kit comprising: a reverse transcription primer comprising (i) a sequence that is substantially complementary to a portion of the target nucleic acid and (ii) a first adaptor sequence; a reverse transcriptase; and an oligonucleotide comprising a second adaptor sequence or a complement thereof.

Embodiment 32 is the kit of Embodiment 31, wherein the kit further comprises a ligase.

Embodiment 33 is the kit of Embodiment 30 or 31, wherein the reverse transcriptase is a reverse transcriptase with terminal transferase activity.

Embodiment 34 is the kit of any one of Embodiments 31-33, wherein the second adaptor sequence or the complement thereof is a TSO or a complement thereof.

Embodiment 35 is the kit of any one of Embodiments 31-34, wherein the kit further comprises an array, wherein the array comprises an attached capture probe comprising in a 5' to a 3' direction: (i) a spatial barcode and (ii) a capture domain that binds specifically to the second adaptor sequence.

Embodiment 36 is a nucleic acid comprising, in the 5' to 3' direction: a spatial barcode; a sequence complementary to a second adaptor sequence; a sequence present in a target nucleic acid; and a sequence complementary to a first adaptor sequence.

Embodiment 37 is a nucleic acid comprising, in the 3' to 5' direction: a complement of a spatial barcode; a second adaptor sequence; a sequence complementary to a sequence present in a target nucleic acid; and a first adaptor sequence.

Embodiment 38 is the nucleic acid of Embodiment 36 or 37, wherein the second adaptor sequence comprises a TSO.

Embodiment 39 is the nucleic acid of Embodiment 36 or 37, wherein the second adaptor sequence comprises a complement of a TSO.

Embodiment 40 is the nucleic acid of any one of Embodiments 36-39, wherein the first adaptor sequence is a reverse transcriptase primer.

What is claimed is:

1. A method of identifying a location of a target nucleic acid in a permeabilized tissue section, the method comprising:
    (a) generating a cDNA molecule comprising a sequence that is substantially complementary to the target nucleic acid using a reverse transcription primer comprising (i) a sequence that is substantially complementary to a portion of the target nucleic acid and (ii) a first adaptor sequence, wherein the step of generating the cDNA molecule occurs within the permeabilized tissue section;
    (b) ligating a second adaptor sequence to a 3' end of the cDNA molecule, wherein the step of ligating is performed within the tissue section;
    (c) releasing the cDNA molecule ligated to the second adaptor sequence from the target nucleic acid in the tissue section, such that the second adaptor sequence contacts an array, wherein the array comprises an attached capture probe comprising in a 5' to a 3' direction: (i) a spatial barcode and (ii) a capture domain that hybridizes to the second adaptor sequence ligated to the cDNA molecule;
    (d) extending a 3' end of the capture probe using the cDNA molecule as a template; and
    (e) determining (i) all or a part of the sequence of the target nucleic acid, or a complement thereof, and (ii) the sequence of the spatial barcode, or a complement thereof, and using the determined sequences of (i) and (ii) to identify the location of the target nucleic acid in the permeabilized tissue section.

2. A method of identifying a location of a target nucleic acid in a permeabilized tissue section, the method comprising:
    (a) generating a cDNA molecule comprising a sequence that is substantially complementary to the target nucleic acid using a reverse transcription primer comprising (i) a sequence that is substantially complementary to a portion of the target nucleic acid and (ii) a first adaptor sequence, wherein the step of generating the cDNA molecule occurs within the permeabilized tissue section;
    (b) extending a 3' end of the cDNA molecule to include a second adaptor sequence thereby generating an extended cDNA molecule, wherein the step of extending is performed within the tissue section;
    (c) releasing the extended cDNA molecule from the target nucleic acid, such that the extended cDNA molecule contacts an array, wherein the array comprises an attached capture probe comprising in a 5' to a 3' direction: (i) a spatial barcode and (ii) a capture domain that binds to the second adaptor sequence of the extended cDNA molecule;
    (d) extending a 3' end of the capture probe using the extended cDNA molecule as a template; and
    (e) determining (i) all or a part of the sequence of the target nucleic acid, or a complement thereof, and (ii) the sequence of the spatial barcode, or a complement thereof, and using the determined sequences of (i) and (ii) to identify the location of the target nucleic acid in the permeabilized tissue section.

3. The method claim 1, wherein steps (a) through (c) are performed when the tissue section is disposed on the array.

4. The method of claim 1, wherein step (a) is performed when the tissue section is not disposed on the array and step (b) is performed when the tissue section is disposed on the array, and wherein the method further comprises between steps (a) and (b), a step of disposing the tissue section on the array.

5. The method of claim 1, wherein steps (a) and (b) are performed when the tissue section is not disposed on the array, and wherein the method further comprises between steps (b) and (c), a step of disposing the tissue section on the array.

6. The method of claim 1, wherein the sequence that is substantially complementary to a portion of the target nucleic acid present in the reverse transcription primer comprises a poly(T) sequence.

7. The method of claim 1, wherein the sequence that is substantially complementary to a portion of the target nucleic acid present in the reverse transcription primer comprises a random sequence.

8. The method of claim 1, wherein the second adaptor sequence is a template switching oligonucleotide (TSO), or a complement thereof.

9. The method of claim 1, wherein the capture probe further comprises a unique molecular identifier (UMI).

10. The method of claim 1, wherein the determining in step (e) comprises sequencing (i) all or a part of the sequence of the target nucleic acid, or a complement thereof, and (ii) the sequence of the spatial barcode, or a complement thereof.

11. The method of claim 10, wherein the sequencing is high throughput sequencing.

12. The method of claim 10, wherein the sequencing is sequencing by hybridization.

13. The method of claim 1, wherein the target nucleic acid is RNA.

14. The method of claim 13, wherein the RNA is an mRNA.

15. The method of claim 1, wherein the method further comprises, prior to step (a), a step of permeabilizing the tissue section.

16. The method of claim 1, wherein step (a) comprises introducing a reverse transcriptase, dNTPs, and the reverse transcription primer into the permeabilized tissue section.

* * * * *

UNITED STATES PATENT AND TRADEMARK OFFICE
CERTIFICATE OF CORRECTION

PATENT NO.        : 11,891,654 B2
APPLICATION NO.   : 17/184117
DATED             : February 6, 2024
INVENTOR(S)       : Luigi Jhon Alvarado Martinez and Eswar Prasad Ramachandran Iyer Page 1 of 1

It is certified that error appears in the above-identified patent and that said Letters Patent is hereby corrected as shown below:

In the Claims

Column 32, Approximately Line 16, in Claim 3, after "method" insert -- of --.

Signed and Sealed this
Ninth Day of April, 2024

Katherine Kelly Vidal
*Director of the United States Patent and Trademark Office*